United States Patent [19]

Klein et al.

[11] Patent Number: 5,332,726
[45] Date of Patent: * Jul. 26, 1994

[54] ANTITHROMBOTIC PEPTIDES AND PSEUDOPEPTIDES

[75] Inventors: Scott I. Klein, Mont Clare; Bruce F. Molino, Hatfield; Mark Czekaj, Sellersville; Charles Gardner, Royersford; Michael R. Becker, Norristown; Jeffrey M. Dener, King of Prussia; Jeffrey C. Pelletier, Lansdale, all of Pa.

[73] Assignee: Rhone-Poulenc Rorer Pharmaceuticals Inc., Collegeville, Pa.

[*] Notice: The portion of the term of this patent subsequent to Aug. 28, 2007 has been disclaimed.

[21] Appl. No.: 859,779

[22] Filed: Mar. 30, 1992

Related U.S. Application Data

[63] Continuation-in-part of Ser. No. 677,006, Mar. 28, 1991, abandoned, which is a continuation-in-part of Ser. No. 534,385, Jun. 7, 1990, abandoned, which is a continuation-in-part of Ser. No. 460,777, Jan. 4, 1990, abandoned, which is a continuation-in-part of Ser. No. 415,006, Sep. 29, 1989, Pat. No. 4,952,562, which is a continuation-in-part of Ser. No. 534,385, Jun. 7, 1990, abandoned, which is a continuation-in-part of Ser. No. 415,006, Sep. 29, 1990, U.S. Patent No. 4,952,562, which is a continuation-in-part of 460,777, Jan. 4, 1990, abandoned, which is a continuation-in-part of 415,006, Sep. 29, 1989, U.S. Pat. No. 4,952,562.

[51] Int. Cl.$^5$ .................. C07K 5/06; C07K 5/08; C07K 5/10; A61K 37/02
[52] U.S. Cl. .................. 514/18; 514/19; 514/20; 530/331; 562/560; 562/571
[58] Field of Search .............. 514/18, 19, 20; 530/331; 562/560, 571

[56] References Cited

U.S. PATENT DOCUMENTS

| | | | |
|---|---|---|---|
| 3,821,188 | 6/1974 | McKinley et al. | 530/331 |
| 4,629,736 | 12/1986 | Tsukamoto et al. | 514/19 |
| 4,683,291 | 7/1987 | Zimmerman et al. | 530/324 |
| 4,857,508 | 8/1989 | Adams et al. | 514/18 |
| 4,879,313 | 11/1989 | Tjoeng et al. | 514/20 |
| 4,952,562 | 8/1990 | Klein et al. | 514/18 |
| 4,992,463 | 2/1991 | Tjoeng et al. | 549/76 |
| 5,023,233 | 6/1991 | Nutt et al. | 514/11 |
| 5,037,808 | 8/1991 | Tjoeng et al. | 514/20 |
| 5,053,392 | 10/1991 | Klein et al. | 514/18 |
| 5,053,393 | 10/1991 | Tjoeng et al. | 514/18 |
| 5,064,814 | 11/1991 | Klein et al. | 514/18 |
| 5,086,069 | 2/1992 | Klein et al. | 514/399 |
| 5,091,396 | 2/1992 | Tjoeng et al. | 546/332 |
| 5,260,277 | 11/1993 | McKenzie | 514/20 |

FOREIGN PATENT DOCUMENTS

| | | |
|---|---|---|
| 0255206 | 2/1988 | European Pat. Off. |
| 0317278 | 5/1989 | European Pat. Off. |
| 0319506 | 6/1989 | European Pat. Off. |
| 0342962 | 11/1989 | European Pat. Off. |
| 0378432 | 7/1990 | European Pat. Off. |
| 0445796 | 9/1991 | European Pat. Off. |
| 0452257 | 10/1991 | European Pat. Off. |
| 2608160 | 6/1988 | France . |
| 2091270 | 7/1982 | United Kingdom . |
| 2091270A | 7/1982 | United Kingdom . |
| WO91/07976 | 6/1991 | World Int. Prop. O. |

OTHER PUBLICATIONS

Haverstick et al., *Blood*, vol. 66, No. 4, pp. 946–952, Oct. 1985, "Inhibition of Platelet Adhesion to Fibronectinb, Fibrinogen, and von Willebrand Factor Substrates".

(List continued on next page.)

*Primary Examiner*—Robert A. Wax
*Assistant Examiner*—Stephen Walsh
*Attorney, Agent, or Firm*—Paul R. Darkes; Martin F. Savitzky

[57] ABSTRACT

This invention relates to novel peptide and pseudopeptide derivatives and analogs of aspartic acid which are useful as inhibitors of platelet aggregation and thrombus formation in mammalian blood, to pharmaceutical compositions including such compounds, and to their use in inhibiting thrombus formation and platelet aggregation in mammals.

21 Claims, No Drawings

OTHER PUBLICATIONS

Plow et al., *Proc. Natl. Sci. USA*, vol. 79, pp. 3711–3715, Jun. 1982, Biochemistry, "Inhibition of Fibrinogen Binding to Human Platelets by the Tetrapeptide Glycyl-L-prolyl-L-arginyl-L- ... ".

Plow et al. *Proc. Natl. Acad. Sci. USA*, vol. 82, pp. 8057–8061, Dec. 1985, Cell Biol., "The Effect of Arg--Gly-Asp-containing Peptides on Fibrinogen and von Willebrand Factor Binding ... ".

Fujimura et al., *J. Biol. Chem.*, vol. 261, No. 1, pp. 381–385, Jan. 5, 1986, "von Willebrand Factor: A Reduced and Alkylated 52/48-kDa Fragment Beginning at Amino Acid ... ".

Humphries et al., *Science*, vol. 233, pp. 467–470, Jul. 25, 1986, "A Synthetic Peptide from Fibronectin Inhibits Experimental Metastasis of Murine Melanoma Cells".

Cheresh et al., *J. Biol. Chem*, vol. 262, No. 36, Dec. 25, 1987, pp. 17703–17711, "Biosynthetic and Functional Properties of an Arg-Gly-Asp-directed Receptor Involved in Human ... ".

Ginsberg et al., *J. Biol. Chem.*, vol. 260, No. 7, pp. 3931–3936, Apr. 10, 1985, "Inhibition of Fibronectin Binding to Platelets by Proteolytic Fragments and Synthetic Peptides Which ... ".

Ruggeri et al., *Proc. Natl. Sci. USA*, vol. 83, pp. 5708–5712, Aug. 1986, Med. Sci., "Inhibition of Platelet Function with Synthetic Peptides Designed to be High--Affinity Antagonists of Fibrinogen ... ".

Gartner et al., *J. Biol. Chem.*, vol. 260, No. 22, pp. 11891–11894, Oct. 5, 1985, "The Tetrapeptide Analogue of the Cell Attachment Site of Fibronectin Inhibits Platelet Aggregation and Fibrinogen ... ".

Santoro et al., *Cell*, vol. 48, 867–873, Mar. 13, 1987, "Competition for Related but Nonidentical Binding Sites on the Glycoprotein IIb-IIIa Complex by Peptides Derived ... ".

Parsons (ed.), *Peptide Hormones*, pp. 1–7, University Park Press, Baltimore, Md., (1976), "Characteristics of the Amino Acids as Components of a Peptide Hormone Sequence".

Dayhoff, *Atlas of Protein Sequence and Structure*, vol. 5, pp. 89–99, (1972).

ANTITHROMBOTIC PEPTIDES AND PSEUDOPEPTIDES

This application is a continuation-in-part of U.S. Ser. No. 07/677,006, filed Mar. 28, 1991, now abandoned, which is a continuation-in-part application of U.S. Ser. No. 07/534,385, filed Jun. 7, 1990, now abandoned, and of U.S. Ser. No. 07/460,777, filed Jan. 4, 1990, now abandoned, and which is also a continuation-in-part of Ser. No. PCT/US90/05448, filed Sep. 25, 1990, which is a continuation-in-part of U.S. Ser. No. 07/415,006, filed Sep. 29, 1989, now U.S. Pat. No. 4,952,562, issued Aug. 28, 1990; and this application is a continuation-in-pad of U.S. Ser. No. 07/534,385, filed Jun. 7, 1990, now abandoned, which is in turn a continuation-in-part of U.S. Ser. No. 07/415,006, filed Sep. 29, 1989, now U.S. Pat. No. 4,952,562, issued Aug. 28, 1990, and of U.S. Ser. No. 07/460,777, filed Jan. 4, 1990, now abandoned; and this application is a continuation-in-part of PCT/US90/05448, filed Sep. 25, 1990, which is in turn a continuation-in-part of U.S. Ser. No. 07/415,006, filed Sep. 29, 1989, now U.S. Pat. No. 4,952,562, issued Aug. 28, 1990.

BACKGROUND OF INVENTION

1. Field of the Invention

This invention relates to compounds having antithrombotic activity. More particularly, the invention relates to novel peptides and pseudopeptides that inhibit platelet aggregation and thrombus formation in mammalian blood and are useful in the prevention and treatment of thrombosis associated with disease states such as myocardial infarction, stroke, peripheral arterial disease and disseminated intravascular coagulation.

Haemostasis, the biochemistry of blood coagulation, is an extremely complex and as yet not completely understood phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of platelet adhesive glycoproteins, i.e., fibrinogen, fibronectin, and von Willebrand factor. Fibrinogen is a co-factor for platelet aggregation, while fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane protein complex known as glycoprotein IIb/IIIa.

Adhesive glycoproteins, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. Compounds within the scope of the present invention block the fibrinogen receptor, thus inhibiting platelet aggregation and subsequent thrombus formation and when administered in the form of pharmaceutical compositions comprising such compounds are useful for the prevention and treatment of thrombogenic diseases, such as myocardial infarction, stroke, peripheral arterial disease and disseminated intravascular coagulation.

2. Reported Developments

It has been observed that the presence of Arg-Gly-Asp (RGD) is necessary in fibrinogen, fibronectin and von Willebrand factor for their interaction with the cell surface receptor (Ruoslahti E., Pierschbacher, *Cell* 1986, 44, 517–18). Two other amino acid sequences also seem to take part in the platelet attachment function of fibrinogen, namely, the Gly-Pro-Arg sequence, and the dodecapeptide, His-His-Leu-Gly-Gly-Ala-Lys-Gln-Ala-Gly-Asp-Val sequence. Small synthetic peptides containing the RGD or dodecapeptide have been shown to bind to the platelet GPIIb/IIIa receptor and competitively inhibit binding of fibrinogen, fibronectin and von Willebrand factor as well as inhibit aggregation of activated platelets (Plow, et al., *Proc. Natl. Acad. Sci. USA* 1985, 82, 8057–61; Ruggeri, et al., *Proc. Natl. Acad. Sci. USA* 986, 5708–12; Ginsberg, et al., *J. Biol. Chem.* 1985, 260, 3931–36; and Gartner, et al., *J. Biol. Chem.* 1987, 260, 11,891–94).

Indolyl compounds containing guanidinoalkanoyl- and guandinoalkenoyl-aspartyl moieties are reported to be platelet-aggregation inhibitors by Tjoeng, et al., U.S. Pat. Nos. 5,037,808 and 4,879,313.

U.S. Pat. No. 4,992,463 (Tjoeng, et al.), issued Feb. 12, 1991, discloses generically that a series of aryl and aralkyl guanidinoalkyl peptide mimetic compounds exhibit platelet aggregation inhibiting activity and discloses specifically a series of mono- and dimethoxy phenyl peptide mimetic compounds and a biphenylalkyl peptide mimetic compound.

U.S. Pat. No. 4,857,508 (Adams, et al.), issued Aug. 15, 1989, discloses generically that a series of guandinoalkyl peptide derivatives containing terminal aralkyl substituents exhibit platelet aggregation inhibiting activity and discloses specifically a series of O-methyl tyrosine, biphenyl, and naphthyl derivatives containing a terminal amide functionality.

Haverstick, D. M., et al., in *Blood* 66 (4), 946–952 (1985), disclose that a number of synthetic peptides, including arg-gly-asp-ser and gly-arg-gly-asp-ser, are capable of inhibiting thrombin-induced platelet aggregation.

Plow, E. F., et al., in *Proc. Natl. Acad. Sci. USA* 79, 3711–3715 (1982), disclose that the tetrapeptide glycyl-L-prolyl-L-arginyl-L-proline inhibits fibrinogen binding to human platelets.

French Application No. 86/17507, filed Dec. 15, 1986, discloses that tetra-, penta- and hexapeptide derivatives containing the -arg-gly-asp- sequence are useful as antithrombotics.

U.S. Pat. No. 4,683,291 (Zimmerman, et al.), issued Jul. 28, 1987, discloses that a series of peptides, comprised of from six to forty amino acids, which contain the sequence -arg-gly-asp- are platelet binding inhibitors.

European Application Publication No. 0 319 506, published Jun. 7, 1989, discloses that a series of tetra-, penta-, and hexapeptide derivatives containing the -arg-gly-asp- sequence are platelet aggregation inhibitors.

Cyclic peptide analogues containing the moiety Gly-Asp are reported to be fibrinogen receptor antagonists in U.S. Pat. No. 5,023,233.

Peptides and pseudopeptides containing amino-, guanidino-, imidizaloyl-, and/or amidino- alkanoyl, and alkenoyl moieties are reported to be antithrombotic agents in pending U.S. applications Ser. Nos. 07/677,006, 07/534,385, and 07/460,777 filed on Mar. 28, 1991, Jun. 7, 1990, and Jan. 4, 1990, respectively, as well as in U.S. Pat. No. 4,952,562, and in International Application No. PCT/US90/05448, filed Sep. 25, 1990, all assigned to the same assignee as the present invention.

Peptides and pseudopeptides containing amino- and guanidino- alkyl- and alkenyl-benzoyl, phenylalkanoyl, and phenylalkenoyl moieties are reported to be antithrombotic agents in pending U.S. application Ser. No. 07/475,043, filed Feb. 5, 1990, assigned to the same assignee as the present invention.

The present invention relates to novel peptides and pseudopeptides which inhibit platelet aggregation and subsequent thrombus formation.

SUMMARY OF THE INVENTION

Compounds of the present invention are described by Formula I

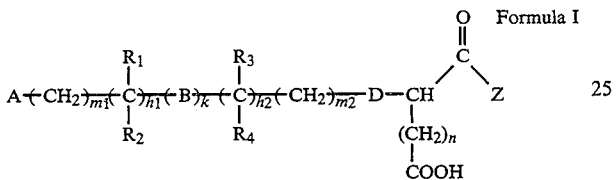

wherein:

A is cyano,

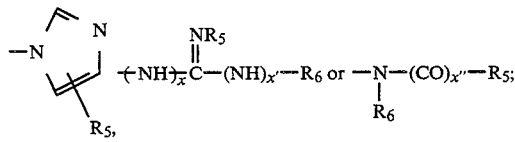

B and D are independently —CH$_2$—NH—, —CH$_2$—S—, —CH$_2$—O—,

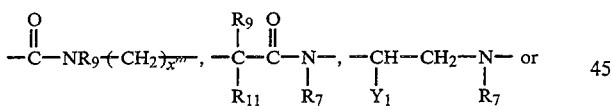

B may also be 5-tetrazol-1-yl, —CR$_7$=CR$_8$—, —CC— or

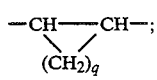

Z is —OR$_a$, nitrogen-containing heterocyclyl, a D- or L-isomer of an α-amino acid bonded at the α-nitrogen, a dipeptide bonded at the N-terminal α-amino acid, or —NR$_a$R$_x$, where R$_x$ is H or

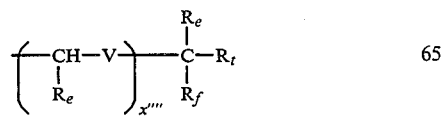

where V is

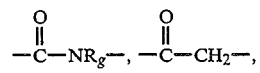

—(CH$_2$)$_p$—, —CH=CH—, —CH$_2$NH—, —CH$_2$—O—, or —CH$_2$—S—;

R$_e$ and R$_f$ are independently H, alkyl, cycloalkyl, cycloalkylmethyl, or —(CH$_2$)$_s$—R$_z$ where R$_z$ is nitrogen-containing heterocyclylcarbonyl, —COOR$_n$, —OR$_n$, —SR$_n$—, —NR$_n$R$_o$,

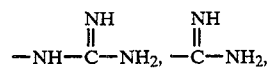

phenyl, substituted phenyl, naphth-1-yl, naphth-2-yl, substituted napth-1-yl, substituted naphth-2-yl, 1,1-diphenylmethyl, 1,1-di(substituted phenyl)methyl, N—R$_n$ substituted indol-2-yl, N—R$_n$ substituted indol-3-yl, substituted (N—R$_n$ substituted)indol-2-yl, substituted (N—R$_n$ substituted)indol-3-yl, quinolin-2-yl, quinolin-3-yl, quinolin-4-yl, substituted quinolin-2-yl, substituted quinolin-3-yl, substituted quinolin-4-yl, N—R$_n$ substituted imidazol-2-yl, N—R$_n$ substituted imidazol-4-yl, N—R$_n$ substituted imidazol-5-yl, substituted N—R$_n$ substituted imidazol-2-yl, substituted N—R$_n$ substituted imidazol-4-yl, substituted N—R$_n$ substituted imidazol-5-yl, imidizol-1-yl, or substituted imidazol-1-yl;

R$_{1-10}$, R$_a$, R$_g$, R$_k$, R$_{m-p}$, R$_q$, and R$_s$ are independently H, alkyl, cycloalkyl, cycloalkylmethyl, aryl, substituted aryl, aralkyl or substituted aralkyl;

R$_t$ is —H, —COOH, —COOR$_k$, carbamoyl, N-containing heterocyclyl or

R$_n$ is R$_{10}$ or Y$_1$;
Y$_1$ is H, amino or

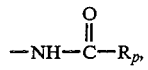

it being understood that Y$_1$ may be the same or different for B and D;

x, x', x", x''' and x'''' are independently 0 or 1; m$_1$ and m$_2$ are independently 0 to 9; h$_1$, h$_2$, and k are independently 0 or 1; n is 1 to 3; q is 1 to 5; and p and s are independently 0 to 6;

provided that when A is guanidino, and B and D are —C(O)NH—, then Z is other than aralkylamino or substituted aralkylamino; and when A is guanidino, B and D are —C(O)NH—, and Z is —NR$_a$R$_x$ where R$_x$ is

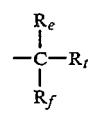

and $R_t$ is —C(O)NH$_2$ and $R_e$ is hydrogen, then $R_f$ is other than benzyl, substituted benzyl, naphthylmethyl or substituted naphthylmethyl; and when

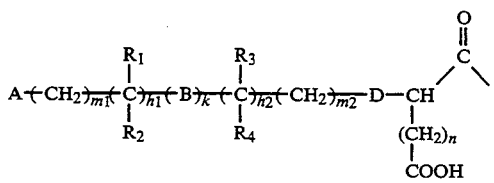

is arginyl-glycyl-aspartyl, then Z is other than a naturally occurring amino acid or a dipeptide composed of two naturally occurring amino acids;
and pharmaceutically acceptable salts thereof.

Additionally, this invention relates to pharmaceutical compositions comprising such compounds, and to methods of treatment of abnormal thrombus formation in mammals comprising the administration of such compounds and pharmaceutical compositions.

DETAILED DESCRIPTION OF THE INVENTION

As used above, and throughout the description of this invention, the following terms, unless otherwise indicated, shall be understood to have the following meanings:

"Nitrogen-containing heterocyclyl" means about a 4- to about a 15-membered nitrogen-containing monocyclic or multicyclic ring system in which one or more of the other atoms in the ring or rings may be an element other than carbon, for example nitrogen, oxygen or sulfur and further that the heterocycle is bound at the nitrogen atom. Preferred nitrogen-containing heterocyclyl groups include pyrrolidin-1-yl, piperidin-1-yl, homopiperidin-1-yl, morpholin-4-yl, 1,2,3,4-tetrahydroisoquinolin-2-yl, piperazin-1-yl. In the case of piperazin-1-yl, the nitrogen at the 4-position preferably may be substituted by alkyl, cycloalkyl, cycloalkylmethyl, aryl, substituted aryl, aralkyl or substituted arakyl.

"α-amino acid" means a synthetic or naturally occurring amino acid. Preferred α-amino acids are the naturally occurring amino acids, i.e. glycine, alanine, valine, leucine, isoleucine, serine, threonine, phenylalanine, tyrosine, tryptophan, cysteine, methionine, proline, hydroxyproline, aspartic acid, aspargine, glutamine, glutamic acid, histidine, arginine, ornithine, and lysine.

"Dipeptide" means α-aminoacyl-α-aminoacid.

"Carboxy" means a —COOH group.

"Carbamoyl" means a

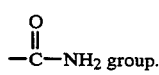

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain. Preferred straight or branched alkyl groups are the "lower alkyl" groups which are those alkyl groups having from 1 to about 6 carbons.

"Cycloalkyl" means a saturated carbocyclic group having about 3 to about 8 carbon atoms. Preferred cycloalkyl groups include cyclopropyl, cyclobutyl, cyclopentyl, and cyclohexyl.

"Guanidino" means an

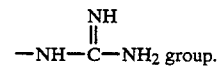

"Aryl" means a phenyl or naphthyl group.

"Substituted aryl" means a phenyl or naphthyl group substituted by one or more aryl group substituents which may be the same or different, where "aryl group substituent" includes alkyl, alkenyl, alkynyl, aryl, aralkyl, hydroxy, alkoxy, aryloxy, aralkoxy, hydroxyalkyl, acyl, formyl, carboxy, alkenoyl, aroyl, halo, nitro, trihalomethyl, cyano, alkoxycarbonyl, aryloxycarbonyl, aralkoxycarbonyl, acylamino, aroylamino, carbamoyl, alkylcarbamoyl, dialkylcarbamoyl, arylcarbamoyl, aralkylcarbamoyl, alkylsulfonyl, alkylsulfinyl, arylsulfonyl, arylsulfinyl, aralkylsulfonyl, aralkylsulfinyl, or —NRR' where R and R' are independently hydrogen, alkyl, aryl, or aralkyl.

"Substituted"-phenyl, naphth-1-yl, naphth-2-yl 1,1-diphenylmethyl, 1,1-di(substituted phenyl)methyl, indol-2-yl, indol-3-yl, quinolin-2-yl, quinolin-3-yl, quinolin-4-yl, imidazol-2-yl, imidazol-4-yl, imidazol-5-yl, and imidazol-1-yl means that these groups are substituted by an aryl group substituent. Preferred aryl group substitutents for these groups are hydrogen, halo, nitro, trihalomethyl, phenyl, alkyl, nitrogen-containing heterocyclyl carbonyl, nitrogen-containing heterocyclyl carbonylalkyl, amidino, guanidino, —NR$_q$R$_s$, —SR$_q$, —COOR$_q$, —NHSO$_2$R$_q$,

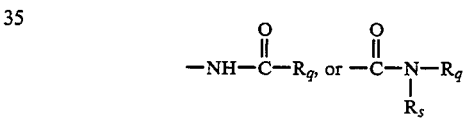

where $R_q$ and $R_s$ are independently H, alkyl, cycloalkyl, cycloalkylmethyl, aryl, substituted aryl, aralkyl or substituted aralkyl.

"Aralkyl" means an alkyl group substituted by an aryl radical. Preferred aralkyl groups include benzyl and phenethyl.

"Substituted aralkyl" means an aralkyl group substituted on the aryl portion by one or more aryl group substituents.

A preferred class of compounds of the present invention is described by Formula I wherein:

B and D are independently —CH$_2$—NH—, —CH$_2$—S—, —CH$_2$—O—,

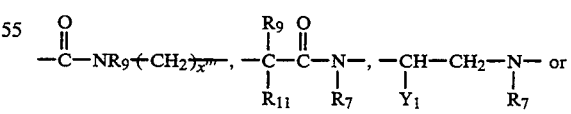

B may also be —CR$_7$═CR$_8$—, —CC— or

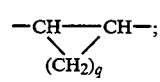

and $R_z$ is nitrogen-containing heterocyclylcarbonyl, —COOR$_n$, —OR$_n$, —SR$_n$—, —NR$_n$R$_o$, $$-NH-\overset{NH}{\underset{\|}{C}}-NH_2, \text{ or } -\overset{NH}{\underset{\|}{C}}-NH_2.$$

Another preferred class of compounds of the present invention is described by Formula I wherein:

B and D are independently —CH$_2$—NH—, —CH$_2$—S—, —CH$_2$—O—, $$-\overset{O}{\underset{\|}{C}}-NR_9(CH_2)_{x'''}, \quad -\overset{R_9}{\underset{R_{11}}{C}}-\overset{O}{\underset{\|}{C}}-\overset{}{\underset{R_7}{N}}-, \quad -CH-CH_2-\overset{}{\underset{R_7}{N}}- \text{ or }$$
$$\phantom{xxxxxxxxxxxxxxxxxxxxxxxxxxxxxxxxxxx} \overset{}{\underset{Y_1}{}}$$

$$-\overset{}{\underset{Y_1}{CH}}-CH_2-O-;$$

B may also be —CR$_7$=CR$_8$—, —CC— or $$-CH\underset{(CH_2)_q}{\overset{}{---}}CH-;$$

and $R_z$ is nitrogen-containing heterocyclylcarbonyl, —COOR$_n$,—OR$_n$, —SR$_n$—, —NR$_n$R$_o$, $$-NH-\overset{NH}{\underset{\|}{C}}-NH_2, \text{ or } -\overset{NH}{\underset{\|}{C}}-NH_2; \text{ and}$$

Z is —OR$_a$, pyrrolidin-1-yl, piperidin-1-yl, homopiperidin-1-yl, morpholin-4-yl, piperazin-1-yl, a D- or L-isomer of an α-amino acid bonded at the α-nitrogen, a dipeptide bonded at the N-terminal α-amino acid, or —NR$_a$R$_x$ where R$_x$ is H or $$-\left(\overset{R_e}{\underset{R_e}{CH}}-V\right)_{x'''}-\overset{R_e}{\underset{R_f}{C}}-R_{f'}.$$

Another preferred class of compounds of the present invention is described by Formula II Formula II
$$NH_2-\overset{NH}{\underset{\|}{C}}-NH(CH_2)_{m1}\overset{O}{\underset{\|}{C}}-NH-CH_2-\overset{O}{\underset{\|}{C}}-NH-\underset{\underset{COOH}{\underset{\|}{CH}}}{\overset{}{CH}}-\overset{O}{\underset{\|}{C}}-Z$$

wherein:
$m_1$ is 2 to 9; and
Z is phenethylamino or 1,2,3,4-tetrahydroisoquinolin-2-yl.

Still another preferred class of compounds of the present invention is described by Formula I wherein:
B is 5-tetrazolyl-1-yl; and
R$_z$ is wherein:
W$_1$ and W$_2$ are independently hydrogen, halo, nitro, trihalomethyl, phenyl, alkyl, nitrogen-containing heterocyclyl carbonyl, nitrogen-containing heterocyclyl carbonylalkyl, amidino, guanidino, —NR$_q$R$_s$, —SR$_q$, —COOR$_q$, $$-NH-\overset{O}{\underset{\|}{C}}-R_q, \text{ or } -\overset{O}{\underset{\|}{C}}-\overset{}{\underset{R_s}{N}}-R_q;$$

and
R$_n$, R$_q$ and R$_s$ are independently H, alkyl, cycloalkyl, cycloalkylmethyl, aryl, substituted aryl, aralkyl or substituted aralkyl.

A more preferred class of compounds of the present invention is described by Formula III Formula III
$$A(CH_2)_{\overline{m1}}(B)_{\overline{k}}(CH_2)_{\overline{m2}}\overset{O}{\underset{\|}{C}}-NH-\underset{\underset{COOH}{\underset{|}{CH_2}}}{\overset{}{CH}}\diagdown \overset{O}{\underset{\|}{C}}\diagdown Z$$

wherein:
A is guanidino or $$-N\underset{\underset{R_5}{}}{\overset{\diagup\diagdown N}{\diagdown\diagup}};$$

$m_1$ is 1 to 9;
$m_2$ is 0 or 1; and

B is —CH=CH— or

A still more preferred class of compounds of the present invention is described by the more preferred class of compounds wherein A is guanidino.

A most preferred class of compounds of the present invention is described by the still more preferred class of compounds wherein Z is a D- or L-isomer of an α-amino acid bonded at the α-nitrogen, or Z is a dipeptide bonded at the N—terminal α-amino acid.

Another most preferred class of compounds of the present invention is described by the still more preferred class of compounds wherein Z is a D- or L-isomer of an α-amino acid bonded at the α-nitrogen.

A particularly preferred special embodiment of the present invention is described by the still more preferred class of compounds wherein Z is a D- or L-isomer of an α-amino acid bonded at the α-nitrogen, said α-amino acid being selected from the group consisting of glycine, alanine, valine, leucine, isoleucine, serine, threonine, phenylalanine, tyrosine, tryptophan, cysteine, methionine, proline, hydroxyproline, aspartic acid, aspargine, glutamine, glutamic acid, histidine, arginine, ornithine, and lysine.

A most preferred special embodiment of the present invention is described by the still more preferred class of compounds wherein Z is a D- or L-isomer of an α-amino acid bonded at the α-nitrogen, said α-amino acid being selected from the group consisting of valine, leucine, isoleucine, and arginine.

Representative compounds of the present invention include:

5-guanidinopentanoyl-N-(ethyl)-glycyl-L-aspartyl-L-leucine;
6-guanidinohexanoyl-N-(ethyl)-glycyl-L-aspartyl-L-leucine;
6-guanidinohexanoyl-N-(ethyl)-glycyl-L-aspartyl-L-isoleucine;
6-guanidinohexanoyl-sarcosyl-L-aspartyl-L-leucine;
6-guanidinohexanoyl-N-(ethyl)-glycyl-L-aspartyl-L-valine;
6-guanidinohexanoyl-sarcosyl-L-aspartyl-L-valine;
5-guanidinovaleroyl-sarcosyl-L-aspartyl-L-valine;
5-guanidinopentanoyl-N-(ethyl)-glycyl-L-aspartyl-L-arginine;
8-guanidinooct-2-enoyl-L-aspartyl-L-valine;
9-guanidinononanoyl-L-aspartyl-L-isoleucine-4-guanidinobutyl amide;
9-guanidinononanoyl-L-aspartyl-L-leucine;
9-guanidinononanoyl-L-aspartyl-L-arginine;
9-guanidinononanoyl-L-aspartyl-L-arginine-isobutyl ester;
9-guanidinononanoyl-L-aspartyl-L-leucyl-arginine;
9-guanidinononanoyl-L-aspartyl-L-valyl-arginine;
N-[N-(9-guanidinononanoyl-L-aspartyl)-2-aminobutanoyl]-L-arginine;
9-guanidinononanoyl-L-aspartyl-L-alanyl-arginine;
9-guanidinononanoyl-L-aspartyl-L-norleucyl-arginine;
9-guanidinononanoyl-L-aspartyl-D-homoisoleucyl-L-arginine;
9-guanidinononanoyl-L-aspartyl-L-phenylalanyl-L-arginine; or
N-(9-guanidinononanoyl-L-aspartyl)-3-amino-2-sec-butylpropionyl-L-arginine of the ditrifluoroacetate salt thereof; or
pharmaceutically acceptable salts thereof.

Compounds of the present invention contain asymmetric centers. These asymmetric centers may independently be in either the R or S configuration. The present invention comprises the individual stereoisomers and mixtures thereof.

The compounds of the present invention may be useful in the form of the free base or acid or in the form of a pharmaceutically acceptable salt thereof. All forms are within the scope of the invention.

Where the compound of the present invention is substituted with a basic moiety, acid addition salts may be formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial antithrombotic properties inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, malonate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial antithrombotic properties inherent in the free acid are not vitiated by side effects ascribable to the cations. Pharmaceutically acceptable salts within the scope of the invention are those derived from the following bases: sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydroxide, carbonate or similar reactive compound of the chosen metal in an aqueous solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

Compounds of this invention may be prepared in accordance with the reaction sequences described below, or can be prepared by methods known in the art. The starting materials used in the preparation of compounds of this invention are known or are commercially available, or can be prepared by known methods or by specific reaction schemes described herein.

The compounds of the present invention may be readily prepared by standard solid phase or solution phase peptide synthesis using starting materials and/or readily available intermediates from chemical supply companies such as Aldrich or Sigma, (H. Paulsen, G. Merz, V. Weichart, "Solid-Phase Synthesis of O-Glycopeptide Sequences", Angew. Chem. Int. Ed. Engl. 27 (1988); H. Mergler, R. Tanner, J. Gosteli, and P. Grogg, "Peptide Synthesis by a Combination of Solid-Phase and Solution Methods I: A New Very Acid-Labile Anchor Group for the Solid-Phase Synthesis of Fully Protected Fragments. Tetrahedron letters 29, 4005 (1988); Merrifield, R. B., "Solid Phase Peptide Synthesis after 25 Years: The Design and Synthesis of Antagonists of Glucagon", Makromol. Chem. Macromol. Symp. 19, 31 (1988)).

A preferred method of preparing compounds of the present invention is by the solid phase method schematically represented as follows:

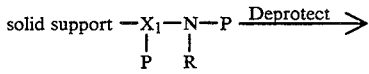

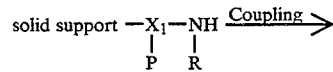

-continued

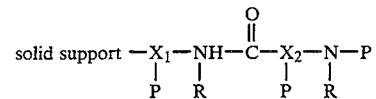

wherein:
the solid support may be, but is not limited to, p-alkoxy benzyl resin, and

is a protected amino acid.

In the synthetic process of making the desired compound the amino acid derivatives are added one at a time to the insoluble resin until the total sequence has been built up on the resin. The functional groups of the amino acid derivatives are protected by blocking groups to prevent cross reaction during the coupling procedure. These blocking groups include N-α-tertiary butyloxycarbonyl (BOC), benzyloxycarbonyl (CBZ), benzyl, t-butyl, 9-fluorenylmethyloxycarbonyl (FMOC), 2-(trimethylsilyl)ethyl, and 4-methoxy-2,3,6-trimethylbenzenesulfonyl. Upon completion of the coupling reaction a functional group is deprotected by standard methods to give an active α-amino function which, in turn, is reacted with a protected amino acid derivative having a free carboxyl function thereon. This procedure is repeated until the desired peptide or pseudopeptide is formed. The compound is then deprotected and removed from the solid support by standard procedures to obtain the final product.

In another preferred method, the compounds of the present invention may be prepared in solution, i.e., without using a solid support. In a manner that is similar to the solid phase synthesis the protected amino acid derivatives or analogs are coupled by using standard procedures, then deprotected to yield the desired final compound.

It may also be desirable or necessary to prevent cross-reaction between other chemically active substituents on reactants. The substituents may be protected by standard blocking groups which may subsequently be removed or retained, as required, by known methods to afford the desired products or intermediates (see, for example, Green, "Protective Groups in Organic Synthesis", Wiley, New York, 1981). Selective protection or deprotection may also be necessary or desirable to allow conversion or removal of existing substituents, or to allow subsequent reaction to afford the final desired product.

The invention is further explained by the following illustrative examples. In the examples, when the carboxyl terminus of a compound ends in an amino acid other than valine, the synthetic process starts with the use of an appropriate commercially available N-α-FMOC-amino acid p-alkoxybenzyl alcohol resin ester. When such is not available, the appropriate N-α-FMOC protected amino acid p-alkoxybenzyl alcohol resin ester is prepared by the procedure of E. Givalt, et al. (Int. J. Peptide Protein Res. 1989, 33,368). Subsequent treatment of the starting materials is described in Example 1.

EXAMPLE 1

L-Arginyl-L-Asparyl-L-Valine 1 g of N-(9-fluorenylmethyloxycarbonyl)-L-valine p-alkoxybenzyl alcohol resin ester (containing 0.56 mmole of amino acid) is shaken with 20 ml of 20% (v/v) piperidine in methylene chloride for 1 hour to remove the FMOC group. The mixture is filtered and the resin washed with methylene chloride. The deprotected resin is treated with 0.92 g of N-FMOC-L-aspartic acid-β-t-butyl ester in 15 ml of dimethylformamide in the presence of 0.43 g 1-(3-dimethylaminopropyl)-3-ethylcarbodiimide hydrochloride (EDC), 0.31 ml triethylamine, and 0.30 g 1-hydroxybenzotriazole (HOBT), for 1½ hours. This is filtered, washed with methylene chloride, and the resulting resin treated with 20% piperidine in methylene chloride as above to remove the FMOC group. The resulting resin derivative is then treated as above with 1.36 g N-α-FMOC-N-ω-( 4-methoxy-2,3,6-trimethylbenzenesulfonyl)-L-arginine in the presence of triethylamine, EDC, and HOBT. The FMOC group is removed as above. The peptide is removed from the resin by treating with 20 ml of 95% trifluoroacetic acid for two hours. The arginine residue is deprotected by overnight treatment with concentrated trifluoroacetic acid. The resulting solution is diluted with 0.5% acetic acid, washed with 3 portions of ethyl acetate, then lyophilized to give L-arginyl-L-aspartyl-L-valine as the ditrifluoroacetate salt; m.p. 90°-95° C.

EXAMPLE 2

L-Arginylglycyl-L-Aspartyl-α-Isobutylamide

A. 1.16 g of 1-(3-dimethylaminopropyl)-3-ethylcarbodiimide hydrochloride (EDC) and 0.93 ml of triethylamine are stirred together in 50 ml of methylene chloride for 10 minutes. 2.5 g N-α-(FMOC)-L-aspartic acid β-t-butyl ester, 0.60 ml isobutylamine and 0.82 g hydroxybenzotriazole (HOBT) are added and the solution stirred at room temperature overnight. The solution is diluted with ethyl acetate, washed twice with water and dried over magnesium sulfate. The filtered solution is evaporated in vacuo to give 2.2 g N-α-(FMOC)-L-aspartic acid isobutyl amide β-butyl ester.

B. The amide obtained in Example 2A is dissolved in 20% (v/v) piperidine in methylene chloride and stirred at room temperature for 2 hours. The solution is evaporated in vacuo and the residue dissolved in ethyl acetate and this solution is washed with 10% sodium bicarbonate solution, dried over sodium sulfate, filtered and evaporated to give 1.7 g L-aspartic acid-α-isobutyl amide-β-t-butyl ester.

C. 0.67 g N-α-FMOC glycine and 0.55 g of the amide obtained in 2B are treated under the conditions of Example 2A to give N-α-(FMOC)-glycyl-L-aspartic acid isobutyl amide-β-butyl ester.

D. The product obtained in Example 2C is treated as in Example 2B to remove the FMOC protecting group to give glycyl-L-aspartic acid isobutyl amide-β-butyl ester.

E. 0.40 g of the product of Example 2D and 0.78 g N-α-t-BOC-N-ω-(4-methoxy-2,3,6-trimethylbenzenesulfonyl)-L-arginine are treated as in Example 2A with 0.29 g EDC, 0.17 g HOBT and 0.18 ml triethylamine to give N-α-BOC-N-(4-ω-methoxy-2,3,6-trimethylbenzenesulfonyl)-L-arginylglycyl-L-aspartic acid isobutyl amide-β-butyl ester.

F. 0.35 g of the product obtained in Example 2E is treated with concentrated trifluoroacetic acid in the presence of two drops of ethanedithiol overnight. The solution is diluted with 0.5% acetic acid and washed with 4×100 ml of ethyl acetate. The aqueous solution was lyophilized to 0.19 g of a white solid, L-arginylglycyl-L-aspartyl-α-isobutylamide as the ditrifluoroacetate salt; m.p. 90°-95° C.

EXAMPLE 3

L-Ornithylglycyl-L-Aspartyl-Valine

A. 1.27 g L-valine t-butyl ester and 2.5 g N-α-FMOC-L-aspartic acid β-t-butyl ester are treated as in Example 2A in the presence of 1.16 g EDC, 0.93 g triethylamine and 0.82 g hydroxybenzotriazole. The resulting product is then deprotected as in Example 2B to give L-aspartyl-β-t-butyl ester-L-valine-α-t-butyl ester.

B. 1. 1 g of the product obtained from Example 3A is treated with N-α-FMOC-glycine in the presence of 0.60 g EDC, and 0.43 g of triethylamine in methylene chloride as in Example 2A and the resulting product deprotected in 20% piperidine in methylene chloride as in Example 2B to give 0.65 g glycyl-L-aspartyl-β-t-butyl ester-L-valine-α-t-butyl ester.

C. 0.25 g of the product from Example 3B is treated with 0.23 g N-α-t-BOC-N-δ-CBZ-ornithine in 5ml of methylene chloride in the presence of 0.12 g EDC, 0.8 g HOBT and 0.09 ml triethylamine as in 2A to give 0.45 g N-α-t-BOC-N-δ-CBZ-L-ornithyl-glycyl-L-aspartyl-L-β-t-butyl ester-L-valine-α-t-butyl ester.

D. The benzyloxycarbonyl protecting group on the product compound of Example 3C is removed by dissolving 0.45 g of the protected compound in 20 ml of cyclohexene and adding 0.10 g 10% palladium on carbon and heating at reflux, under nitrogen, for 2 hours. The resulting solution is filtered, evaporated, and chromatographed on silica gel in chloroform/methanol/water 90:10:3 to give 0.25 g N-α-t-BOC-L-ornithyl-glycyl-L-aspartyl-β-t-butyl ester-L-valine-t-butyl ester.

E. 0.23 g of the product obtained in Example 3D is dissolved in 5 ml trifluoroacetic acid with 3 drops of ethanedithiol added. The solution is stirred for 7 hours, evaporated, and the residue partitioned between ethyl acetate and 0.5M acetic acid. The aqueous portion was separated and lyophilized and the resulting solid purified by HPLC to give L-ornithyl-glycyl-L-aspartyl-L-valine as the ditrifluoroacetate salt; m.p. 122°-25° C.

EXAMPLE 4

L-Arginylsarcosyl-L-Aspartyl-L-Valine

N-α-FMOC-sarcosine is substituted for N-α-FMOC-glycine and the resulting product is treated with piperidine in methylene chloride as in Example 1 to remove the FMOC group. The corresponding product is obtained. Treating this product with the arginine derivative of Example 1, cleaving the resulting peptide from the resin and deprotecting as in Example 1 gave L-arginylsarcosyl-L-aspartyl-L-valine as the ditrifluoroacetate salt; m.p. 145° C. (dec.).

EXAMPLE 5

L-Arginylglycyl-L-Aspartyl-L-(N-Methyl)Valine

A. 1 g of p-alkoxybenzylalcohol resin (0.5–1 mmole/g of resin), 0.706 g of N-FMOC-N-methyl-L-valine, 0.382 g EDC, 0.270 g HOBT, and 0.28 ml triethylamine are combined in 15 ml of dimethylformamide and shaken for 2 hours. The mixture is filtered and the resin washed with DMF. The resin is treated as above for a second time, then shaken with 0.28 ml glacial acetic acid, 0.955 g EDC, and 0.7 ml triethylamine in DMF and deprotection effected with 20% piperidine in methylene chloride as in Example 1. This gives N-Methyl-L-valine-p-alkoxybenzyl resin ester.

B. L-aspartic acid, glycine and L-arginine are coupled and deprotected, sequentially, as in the previous examples and the peptide removed from the resin to give L-arginylglycyl-L-aspartyl-L-(N-methyl)valine as the ditrifluoroacetate salt which decomposes at 153° C.

EXAMPLE 6

L-Arginylglycyl-L-Aspartyl Glycine

Starting with N-α-FMOC-glycine-p-alkoxy benzyl resin ester, sequentially coupling L-aspartic acid, glycine and arginine, deprotecting and removing the peptide as in the above examples, L-arginylglycyl-L-aspartyl glycine is obtained as the ditrifluoroacetate salt; m.p. 85°–90° C.

EXAMPLE 7

N-(L-Arginyl-2-Aminoethyl)-L-Aspartyl-L-Valine

A. 1.18 g EDC and 0.86 ml of triethylamine are combined in 20 ml of methylene chloride and stirred for 10 minutes. 2 g N-α-CBZ-L-aspartic acid β-t-butyl ester, 0.83 g HOBT, 1.3 g L-valine-t-butyl ester and 0.86 ml triethylamine were added and the solution stirred overnight. The solution is diluted with ethyl acetate and washed with 10% citric acid solution, 10% sodium carbonate solution, water, then dried over sodium sulfate, evaporated to give 1.9 g N-α-CBZ-L-aspartyl-t-butyl ester-L-valine-t-butyl ester.

B. 2.2 g of N-α-CBZ-glycine methyl ester is dissolved in 50 ml of anhydrous toluene and cooled to −78° C., under nitrogen. To this is added 13 ml of 1.5M diisobutyl aluminum hydride in toluene over a period of 1 hour. The solution is stirred for an additional hour at −78° C., then quenched by addition of 50 ml 5% hydrochloric acid solution. The solution is extracted with ethyl acetate which is washed with water and dried over sodium sulfate, evaporated to give 1.55 g N-α-CBZ-2-aminoacetaldehyde.

C. The product from Example 7A is deprotected as in Example 3D to give L-aspartyl-t-butyl ester-L-valine-t-butyl ester.

D. 1.55 g of the aldehyde from Example 7B, 3.4 g of the product from Example 7C, 1.64 g sodium acetate, 1.23 g sodium cyanoborohydride and 1 g of 3 Angstrom molecular sieves are stirred together in 100 ml methanol for 3 days. The solution is filtered and 5 ml of 5% hydrochloric acid is added. The solution is diluted with water and adjusted to pH 9 with 10% sodium carbonate, then extracted with water, and dried over sodium sulfate. The solution is evaporated and the residue purified by flash chromatography in ethyl acetate/hexane, 1:1, to give 1.1 g N-CBZ-aminoethyl-L-aspartyl-β-t-butyl ester-L-valine-t-butyl ester.

E. The CBZ group is removed from the product of Example 7D as in Example 3D to give N-aminoethyl-L-aspartyl-t-butyl ester-L-valine-t-butyl ester.

F. The product from Example 7E is coupled with N-α-t-BOC-N-ω-(4-methoxy-2,3,6-trimethylbenzenesulfonyl)-L-arginine as in Example 2D and the resulting product deprotected as in 2E to give N-(L-arginyl-2-aminoethyl)-L-aspartyl-L-valine as the tritrifluoroacetate salt; m.p. 91–5° C.

EXAMPLE 8

L-Arginylglycyl-L-Aspartic Acid α-Benzyl Ester

A. 1 g of N-t-BOC-L-aspartic acid α-benzyl ester is treated with 0.366 g of 2-(trimethylsilyl)ethanol in the presence of 0.592 g EDC, 0.419 g HOBT and 0.43 ml triethylamine in 20 ml of methylene chloride for 2 hours. The product is isolated as in Example 2A to give N-t-BOC-L-aspartic acid α-benzyl ester-β-2-(trimethylsilyl)ethyl ester.

B. The product of Example 8A is deprotected by treating with 10 ml of trifluoroacetic acid in 30 ml of methylene chloride for 2 hours at room temperature. The mixture is cooled to 0° C. and 20 ml of saturated sodium carbonate solution is added dropwise. The layers are separated and the organic layer dried over magnesium sulfate, filtered, evaporated to give L-aspartic acid-α-benzyl ester-β-2-(trimethylsilyl)ethyl ester.

C. The product of Example 8B and N-t-BOC glycine are coupled in a manner similar to that described in the previous examples to give BOC-glycyl-L-aspartic acid-α-benzyl ester-β-2-(trimethylsilyl)ethyl ester.

D. The BOC group is removed from the product of Example 8C as in Example 8B to give glycyl-L-aspartic acid-α-benzyl ester-β-2-(trimethylsilyl)ethyl ester.

E. The product from Example 8D is coupled to N-α-BOC-N-ω-(4-methoxy-2,3,6-trimethylbenzenesulfonyl)-L-arginine as in 2D to give N-α-BOC-N-ω-(4-methoxy-2,3,6-trimethyl-benzenesulfonyl)-L-arginyl-glycylaspartic acid α-benzyl ester-β-2-(trimethylsilyl)ethyl ester.

F. 0.30 g of the product obtained in Example 8E is stirred with 5 ml of trifluoroacetic acid at room temperature for 24 hours. The reaction mixture is then stirred with 0.5N acetic acid and washed with ethyl acetate. The aqueous layer is lyophilized to give L-arginylglycyl-L-aspartic acid α-benzyl ester ditrifluoroacetate; m.p. 85°–7° C.

EXAMPLE 9

N-(6-Aminohexanoyl)-L-Aspartyl-L-Valine

A. 1 g of N-(9-fluorenylmethoxycarbonyl)-L-valine p-alkoxybenzyl alcohol resin ester (containing approximately 0.56 mmol of amino acid) is deprotected by shaking with 10 ml of a solution of 20% piperdine in dimethylformamide for 1.5 hours. The mixture is filtered and the resin derivative washed with methylene chloride to give L-valine p-alkoxybenzyl resin ester.

B. The product from Example 9A is shaken with 0.92 g of N-α-FMOC-L-aspartic acid β-t-butyl ester, 0.3 g of 1-hydroxybenzotriazole (HOBT), 0.43 g of 1-(3-dimethyl-aminopropyl)-3-ethylcarbodiimide hydrochloride (EDC) and 0.32 ml of triethylamine in 10 ml of dimethylformamide for 2 hours. The mixture is filtered and the resin washed with methylene chloride. The resin derivative is then deprotected as in Example 1 to give L-aspartyl-β-t-butyl ester-L-valine p-alkoxybenzyl resin ester.

C. 2 g of 6-aminohexanoic acid and 3.23 g of sodium carbonate are dissolved together in 30 ml of water. The solution is cooled in an ice bath and 3.32 g of di-t-butyl-dicarbonate in 15 ml of tetrahydrofuran is added. The mixture is stirred at room temperature for 5 hours, then diluted with 400 ml of water and extracted with ether. The aqueous solution is acidified to pH 2 with hydrochloric acid and extracted with ethyl acetate. The ethyl acetate layer is dried over magnesium sulfate, filtered and evaporated in vacuo to give N-α-tert-butoxy-carbonyl-6-aminohexanoic acid.

D. The product from Example 9B is shaken with 0.52 g of N-ω-BOC-6-aminohexanoic acid, 0.3 g of HOBT, 0.43 g of EDC and 0.32 ml of triethylamine in 10 ml of dimethylformamide for 17 hours. The mixture is filtered and the resin derivative washed with methylene chloride. The peptide derivative is deprotected and cleaved from the resin by treating with 10 ml of 95% trifluoroacetic acid for 2 hours. The resin is filtered off and the filtrate diluted with 50 ml of 0.5N acetic acid. The aqueous solution is washed with 4×25 ml of ethyl acetate, filtered, then lyophilized to give N-(6-aminohexanoyl)-L-aspartyl-L-valine as the trifluoroacetate salt; m.p. 75°–85° C.

EXAMPLE 10

N-(7-Aminoheptanoyl)-L-Aspartyl-Valine

A. When 7-aminoheptanoic acid is substituted for 6-aminohexanoic acid and treated in a manner similar to that in Example 9C, N-ω-tert-butoxycarbonyl-7-aminoheptanoic acid is obtained.

B. L-aspartyl-β-t-butyl ester-L-valine p-alkoxy-benzyl resin ester (prepared from 1 g of N-FMOC-valine p-alkoxybenzyl resin ester as in Examples 1A and B) is treated with 0.55 g of N-BOC-7-aminoheptanoic acid, with 0.3 g of HOBT, 0.43 g of EDC and 0.32 ml of triethylamine in 10 ml of dimethylformamide in a manner similar to that in Example 9D to give N-(7-aminoheptanoyl)-L-aspartyl-L-valine as the trifluoroacetate salt.

EXAMPLE 11

N-(7-Guanidinoheptanoyl)-L-Aspartyl-L-Valine

A. 7-Guanidinoheptanoic acid is prepared essentially by the method of Miller, et al, *Synthesis*, 777 (1986), which is incorporated herein by reference. 0.50 g of 7-aminoheptanoic acid is dissolved in a solution of 0.475 g of potassium carbonate in 3.5 ml of water. 0.427 g of aminoiminomethanesulfonic acid is added portionwise over 10 minutes and the mixture stirred at room temperature for 24 hours. The resulting solid is collected by filtration. The guanidine is dissolved in diluted hydrochloric acid and the solution evaporated in vacuo. Two portions of 2-propanol are evaporated from the residue to give 7-guanidinoheptanoic acid hydrochloride.

B. L-aspartyl-β-t-butyl ester-L-valine p-alkoxy-benzylalcoholester (prepared from 1 g of N-FMOC-L-valine p-alkoxybenzylalcohol ester resin as in Examples 9A and B) is treated with 0.50 of 7-guanidinoheptanoic acid hydrochloride, 0.3 g of HOBT, 0.43 g of EDC and 0.32 ml of triethylamine in 10 ml of dimethylformamide in a manner similar to that in Example 1D to give N-(7-guanidino-heptanoyl)-L-aspartyl-L-valine as the trifluoroacetate salt; m.p. 75°–80° C.

EXAMPLE 12

N-(8-Guanidinooctanoyl)-L-Aspartyl-L-Valine

A. 8-guanidinooctanoic acid hydrochloride is prepared from 8-aminooctanoic acid in a manner similar to the process used in Example 11A.

B. 0.4 g of 8-guanidinooctanoic acid hydrochloride, L-aspartyl-β-t-butyl ester-L-valine p-alkoxybenzyl resin ester (prepared in the same manner as in Example 1), 0.22 g of HOBT, 0.32 g of EDC and 0.24 ml of triethylamine are shaken in 10ml of dimethylformamide and treated as in Example 9D to give N-(8-guanidinooctanoyl)-L-aspartyl-L-valine as the trifluoroacetate salt.

EXAMPLE 13

If 6-guanidinohexanoic acid hydrochloride is substituted for 7-guanidinoheptanoic acid hydrochloride in Example 11 B, N-(6-guanidinohexanoyl)-L-aspartyl-L-valine is prepared.

EXAMPLE 14

A. If 8-aminooctanoic acid is substituted for 6-aminohexanoic acid in Example 9C, N-tert-butoxycarbonyl-8-aminooctanoic acid is prepared.

B. If N-ω-BOC-8-aminooctanoic acid is substituted for N-ω-BOC-6-aminohexanoic acid in Example 9D, N-(8-amino-octanoyl)-L-aspartyl-L-valine is prepared as the trifluoroacetate salt.

EXAMPLE 15

8-Guanidinooct-2-Enoyl-L-Aspartyl-L-Valine

A. 4 g of 6-amino-1-hexanol is dissolved in 50 ml of 10% aqueous tetrahydrofuran and the solution cooled to 0° C. 7.46 g of di-tert-butyldicarbonate in 25 ml of tetrahydrofuran is added dropwise and the resulting mixture stirred for 3 days at room temperature. The solvent is evaporated in vacuo and the residue dissolved in ethyl acetate. The ethyl acetate solution is washed with water, dried over magnesium sulfate and evaporated in vacuo to give 7.4 g of N-tert-butoxycarbonyl-6-amino-1-hexanol.

B. To a solution of 8.8 g of pyridinium chlorochromate in 250 ml of methylene chloride is added 8.8 g of 3 Angstrom molecular sieves. A solution of 7.4 g of N-tert-butoxycarbonyl-6-amino-1-hexanol in 50 ml of methylene chloride is added dropwise and the mixture stirred at room temperature for 2 hours. The reaction mixture is filtered through silica gel, washing with 40% ethylacetate in hexane, and the filtrate evaporated in vacuo to give 6-N-tert-butoxycarbonylaminohexanal.

C. 1 g of 6-N-tert-butoxycarbonylaminohexanal and 1.54 g of methyl(triphenylphosphoranylidene) acetate are combined in 25 ml of chloroform and the solution refluxed for 2 hours. The solvent is then removed in vacuo and the residue taken up in ether and allowed to stand in the freezer overnight. The resulting suspension is filtered, the filtrate evaporated and the residue flash chromatographed in 20% ethyl acetate in hexane to give methyl-8-N-tert-butoxycarbonylamino-2-octenoate.

D. A solution of 3.2 g of methyl 8-N-tert-butoxycarbonylamino-2-octenoate in 25 ml of methanol and 25 ml of 1 Normal aqueous sodium hydroxide is heated at reflux for 2 hours. The methanol is removed in vacuo and the aqueous solution acidified with 1N hydrochloric acid. The resulting mixture is extracted with ethyl acetate. The organic solution is tided over magnesium sulfate and evaporated to give 8-N-tert-butoxycarbonylamino-2-octenoic acid.

E. 3 g of 8-N-tert-butoxycarbonyl-amino-2-octenoic acid is dissolved in 30 ml of trifluoroacetic acid and the solution stirred at room temperature for 1 hour, then evaporated in vacuo to give 8-amino-2-octenoic acid as the trifluoroacetate salt.

F. 3.1 g of 8-amino-2-octenoic acid trifluoro-acetate is added to 30 ml of water and the pH adjusted to 7 with 1N sodium hydroxide solution. 1.9 g of potassium carbonate is added, then 1.75 g of aminoiminomethane-sulfonic acid is added, portionwise, over 10 minutes. The mixture is stirred for 5 hours at room temperature and the resulting solid collected by filtration. The solid is dissolved in diluted hydrochloric acid and the solution evaporated and two portions of 2-propanol evaporated from the residue to give 8-guanidino-2-octenoic acid hydrochloride.

G. L-aspartyl-β-t-butylester-L-valine p-alkoxybenzyl resin ester (prepared from 0.6 g of N-FMOC-valine p-alkoxybenzyl resin ester as in Examples 1A and B) is treated with 0.33 g of 8-guanidino-2-octenoic acid hydrochloride in the presence of 0.184 g of HOBT, 0.26 g of EDC and 0.19 ml of triethylamine in 10 ml of dimethylformamide in a manner similar to that in Example 1D to give 8-guanidinooct-2-enoyl-L-aspartyl-L-valine as the trifluoroacetate salt.

EXAMPLE 16

6-Guanidinohexanoyl-N-Ethylglycyl-L-Aspartyl-L-Valine

A. If 6-aminohexanoic acid is substituted for 7-aminoheptanoic acid in Example 11A, 6-guanidinohexanoic acid is prepared.

B. To 14.8 g of a 50% aqueous solution of glyoxylic acid is added 50 ml of water. The resulting solution is cooled to 0° C. and treated with 10 ml of a 70% solution of ethylamine in water added by dropwise addition over 15 minutes. The reaction mixture is transferred to a Parr bottle, then 10% palladium on carbon is added and the reaction vessel is shaken under hydrogen at 44 psi for 24 hours. The reaction mixture is filtered through a celite pad and the filtrate is concentrated in vacuo to give a tan oil. The oil is treated with 1N aqueous HCl and concentrated in vacuo to give a solid which is recrystalized from acetic acid.

3.65 g of N-ethyl glycine hydrochloride is stirred in 35 ml of water. This is treated with 8.31 g of sodium carbonate and cooled to 0° C., followed by the dropwise addition of 6.77 g of 9-fluorenylmethyl chloroformate in 15 ml of tetrahydrofuran (THF). The reaction mixture is allowed to slowly warm to room temperature and stirred for 24 hours. The THF is removed in vacuo and the residue is diluted with water and extracted with ether. The aqueous fraction is acidified to pH<2 with 1N aqueous HCl and extracted with ethyl acetate. The organic extracts (ethylacetate) are dried, filtered and concentrated to give N-α-FMOC-N-α-ethyl glycine as a white solid. All FMOC protected substituted glycines are made by this procedure simply by substituting the appropriate amine for ethyl amine in this procedure.

C. N-α-FMOC-N-α-ethyl glycine is substituted for N-α-FMOC glycine and the resulting product is treated with piperidine in methylene chloride as in Example 1 to remove the FMOC groups. N-α-Ethyl glycyl-L-aspartyl-β-t-butyl ester-L-valine-p-alkoxybenzyl alcohol resin ester is obtained.

D. A solution of 0.44 g of 6-guanidinohexanoic acid hydrochloride in 10 ml of DMF is treated with 0.23 g of triethylamine. The solution is cooled to 0° C. and 0.57 g of N,N-bis[2-oxo-3-oxzolinyl]phosphorodiamidic chloride (BOP-Cl) is added in a single portion. The reaction mixture is stirred at 0° C. for 5 minutes and then 1 g of N-α-Ethyl glycyl-L-aspartyl-β-t-butyl ester-L-valine-p-alkoxybenzyl alcohol resin ester is added.
The reaction mixture is shaken for 2 hours at room temperature. The procedure for removal of the peptide from the resin is the same as that described in Example 1. The trifluoroacetate acid solution is diluted with 0.5% acetic acid, washed with 3 portions of ethyl acetate, then lyophilized to give 6-guanidinohexanoyl-N-ethyl glycyl-L-aspartyl-L-valine as a white powder.

EXAMPLE 17

6-(Imidazol-1-yl)-Hexanoyl-N-Ethyl Gycyl-L-Aspartyl-L-Valine

A. A solution of 10 g (51 mmol) of 6-bromohexanoic acid in 100 ml of methanol is treated with anhydrous HCl gas for 5 minutes at room temperature. Concentration in vacuo gives the methyl ester.

A 50 mL round bottom flask is charged with 8 g (38.29 mmol) of 6-bromohexanoic acid methyl ester, 5.7 g (84.24 mmol) of imidazole and 20 mL of THF. The resulting mixture is heated at reflux for 24 hours. Solvent is removed in vacuo and the residue is purified by flash chromatography using 5% methanol/ethyl acetate.

6-(imidazol-1-yl)-hexanoic acid methyl ester is treated with 1N aqueous HCl for 24 hours at reflux to provide, after concentration in vacuo, 6-(imidazol-1-yl)-hexanoic acid hydrochloride.

All corresponding compounds are prepared in a similar fashion starting from the appropriate ω-bromohexanoic acid.

B. When 6-(imidazol-1-yl)-hexanoic acid hydrochloride is substituted for 6-guanidinohexanoic acid hydrochloride and treated in a manner similar to that in Example 16D, 6-(imidazol-1-yl)-hexanoyl-N-ethyl glycyl-L-aspartyl-L-valine is obtained.

EXAMPLE 18

[4-(4'-Guanidinobutyl)Tetrazol-1-yl]-Acetyl-L-Aspartyl-L-Valine

A. N-Phthalyl-5-Aminopentanoyl-Glycine, Methyl Ester

To a stirred suspension of 5.02 g (20.3 mmol) of N-phthalyl-5-aminopentanoic acid and 3.04 g (24.2 mmol) of glycine methyl ester hydrochloride in 100 ml of dry tetrahydrofuran is added 3.27 g (24.3 mmol) of HOBT, 4.65 g (24.3 mmol) of EDC, and 4.94 g (48.8 mmol; 6.80 ml) of triethyl amine in that order. The resulting suspension is stirred for 18 hours, then partitioned between 250 ml of ethyl acetate and 100 ml of water. The layers are separated and the aqueous phase is extracted with 250 ml of ethyl acetate The combined organic layers are washed with 150 ml of 10% aqueous sodium carbonate, then with two 125 ml portions of saturated aqueous sodium chloride. The organic phase is dried (MgSO$_4$) and concentrated in vacuo to give 7.39 g of a white solid. Recrystallization of the product from dichloromethane-hexane gives 6.22 g (96%) of the title compound as a fluffy solid.

B. [4-(N-Phthalyl-4'-Aminobutyl)Tetrazol-1-yl]-Acetic Acid, Methyl Ester

To a stirred suspension of 3.7 g (11.6 mmol) of the protected dipeptide in 65 ml of benzene is added 3.5 g (16.8 mmol) of phosphorus pentachloride in one portion. The suspension is stirred for 2 hours during which time the solids had dissolved. The reaction mixture is concentrated in vacuo to give a light brown oil which is dissolved in 60 ml of a hydrazoic acid solution in benzene. This solution is stirred for 24 hours, concentrated in vacuo and the residue is purified by extraction and chromatography as described before to give 2.89 g (73%) of the desired tetrazole ester as an oil which crystallizes on standing.

C. [4-(N-Phthalyl-4'-Aminobutyl)Tetrazol-1-yl]-Acetic Acid

To a stirred suspension of 2.5 g (7.29 mmol) of the above ester in 99 ml of methanol, cooled in an icewater bath, is added 1.4 g (33.7 mmol) of lithium hydroxide monohydrate in 33 ml of water. The suspension is warmed to 30° C. to dissolve the solids and the solution is stirred at room temperature for 1.5 hours. Acidification of the solution with 12 ml of 6M aqueous hydrochloric acid, followed by work-up as described previously affords 2.39 g (100%) of the tetrazole acid as an unstable white foam.

D. [4-(4'-Aminobutyl)Tetrazol-1-yl]-Acetic Acid, Hydrochloride

To a solution of 2.35 g (7.14 mmol) of the tetrazole acid in 29 ml of ethanol is added 463 mg (450 ml; 7.94 mmol) of 55% aqueous hydrazine. The suspension is heated under reflux for 2.5 hours, cooled to room temperature, and diluted with 30 ml of water. The solution is acidified with 1.36 g (22.7 mmol) of acetic acid, stirred for 2 hours, then boiled for 30 minutes. After cooling the solution in a refrigerator overnight, the precipitate is filtered and washed with 20 ml of cold water. The combined filtrate and washings are concentrated to dryness and the residue (1.98 g) is dissolved in 20 ml of 50% aqueous ethanol and 515 mg (16.1 mmol; 5000 ml) of 55% aqueous hydrazine is added. This solution is heated for 2.5 hours, cooled to room temperature and concentrated to dryness. The residue is stirred with 15 ml of 2N aqueous hydrochloric acid for 13 hours, then the suspension is heated under reflux for 30 minutes. The cooled suspension is filtered and the precipitate is washed with 15 ml of water. The filtrate and washings are concentrated in vacuo to give 3.05 g of the crude amine hydrochloride as a colorless semisolid. Further solid impurities are removed by filtration of the ethanol-soluble material; this gives 1.93 g of a pale yellow oil.

E. [4-(4'-Guanidinobutyl)Tetrazol-1-yl]-Acetic Acid, Hydrochloride

To a stirred solution of 1.85 g (7.92 mmol) of the tetrazole amino acid hydrochloride in 20 ml of water is added 2.3 g (16.6 mmol) of potassium carbonate. To this solution is added 1.18 g (9.52 mmol) of aminoiminomethanesulfonic acid in small portions over a 10 minute period. This solution is stirred for 35 hours and worked up as before to give 1.4 g of the crude guanidino tetrazole acid as an off-white solid. The solid is converted to the hydrochloride by evaporation of a dioxane-aqueous hydrochloric solution of this material to dryness.

F. The peptide coupling of [4-(4'-guanidinobutyl)tetrazol-1-yl]-acetic acid hydrochloride to L-aspartyl-β-t-butyl ester-L-valine p-alkoxybenzyl alcohol resin ester, the cleavage of the resulting peptide from the resin, and the subsequent isolation steps is performed as described in Example 1. The [4-(4'-guanidinobutyl)tetrazol-1-yl]-acetyl-L-aspartyl-L-valine is obtained as the trifluoroacetate salt.

EXAMPLE 19

[5-(5'-Guanidinopentyl)Tetrazol-1-yl]-Acetyl-L-Aspartyl-L-Valine

The desired product is prepared by the procedure described for the preparation of [4-(4'-guanidinobutyl)-tetrazol-1-yl]-acetyl-L-aspartyl-L-valine, by substituting N-phthalyl-6-aminohexanoic acid for N-phthalyl-6-aminopentanoic acid in Example 18A.

EXAMPLE 20

9-Guanidinononanoyl-L-aspartyl-α-benzylphenylalanine

A. BOC-L-phenylalanine (4.74 g, 17.9 mmol), paraformaldehyde (1.65 g, 54.9 mmol), and p-toluenesulfonic acid (0.38 g, 2 mmol) are dissolved in toluene (100 ml) and heated at reflux for two hours while removing water with a Dean-Stark trap. The mixture is allowed to cool, diluted with ether and the organic phase washed with saturated sodium bicarbonate solution, brine, dried over magnesium sulfate, then concentrated in vacuo to give the crude oxazolidinone. The oxazolidinone (4.38 g, 15.8 mmol) is dissolved in tetrahydrofuran (THF) (40 ml) and the solution cooled to $-78°$ C. under a nitrogen atmosphere. A solution of 1M sodium bis(trimethylsilyl)amide (23 ml) in THF is added and the mixture stirred at $-78°$ C. for 30 minutes. Benzyl bromide (2.82 g, 23.7 mmol) is added and stirring continued for 1.5 hours at $-78°$ C. The mixture is quenched with ammonium chloride solution and diluted with ether. The ether solution was washed with saturated sodium bicarbonate solution, brine, dried, and concentrated in vacuo to give the crude dibenzyl oxazolidinone. The dibenzyl oxazolidinone (6.34 g) is dissolved in 85% ethanol/water (100 ml) and sodium hydroxide (1.35 g) is added. The mixture is haeated at reflux for 1 hour, cooled, concentrated in vacuo, and the residue diluted with water and extracted with ethyl acetate. The aqueous layer is acidified with 3N HCl and extracted with ether/ethyl acetate (1:1 ). The organic solution is washed with brine, dried over magnesium sulfate, filtered, and concentrated in vacuo to give BOC-2,2-dibenzyl glycine (3.29 g).

B. BOC-2,2-dibenzyl glycine (3.29 g, 9.25 mmol) is dissolved in a solution of methanol(18 ml) and water (2 ml) and the pH adjusted to 8 with 20% cesium carbonate solution (11 ml). The solution is concentrated in vacuo to dryness and the residue dissolved in dimethylformamide (DMF) (25 ml) and re-concentrated twice and dried under high vacuum. The cesium salt is taken up into DMF (25 ml), benzyl bromide (1.74 g, 10.2 mmol) is added and the mixture stirred at room temperature for 16 hours. The mixture is concentrated in vacuo and the residue diluted with ether. The organic phase is washed with water, brine, dried over magnesium sulfate, and concentrated in vacuo. The crude product is purified by flash chromatography, eluting with 10% ethyl acetate in hexane to give BOC-2,2-dibenzyl glycine benzyl ester.

C. BOC-2,2-dibenzyl glycine benzyl ester is deprotected (trifluoroacetic acid) as in Example 8 and coupled (BOP-Cl) to N-BOC-L-aspartic acid-β-benzyl ester essentially in the manner of Example 16. The resulting dipeptide is, in turn, deprotected (TFA) and coupled (EDC) essentially in the manner of Example 2 to 9-nitroguanidinononanoic acid. Subsequent hydrogenation (H$_2$, Pd/C) gives the desired product, which is isolated as the trifluoroacetate salt, 9-guanidinononanoyl-L-aspartyl-α-benzylphenylalanine, M.S., Cal'd: 568, Found: 568.

EXAMPLE 21

9-Guanidinononanoyl-L-aspartyl-(R,S)-α-isobutylornithine

A. BOC-L-leucine is converted to racemic BOC-(2-isobutyl)-allyl glycine benzyl ester using essentially the procedures of Example 20, Steps A and B, substituting allyl bromide in the alkylation step. The benzyl ester (2.07 g, 5.73 mmol) is dissolved in THF (40 ml), under nitrogen, 0.5M 9-borabicyclo[3.3.1]-nonane (9-BBN)in hexanes (46 ml, 23 mmol) is added and mixture stirred at room temperature for 16 hours. The reaction mixture is quenched with water (1 ml) and a mixture of 1N aqueous sodium hydroxide solution (51 ml) and 30% hydrogen peroxide solution (18 ml) is added dropwise. The mixture is stirred for 1 hour at room temperature, saturated with solid sodium chloride, then extracted with ether. The organic layer is washed with saturated sodium bicarbonate solution, brine, dried over magnesium sulfate, filtered, and concentrated in vacuo. The crude product is purified by flash chromatography, eluting with 20% ethyl acetate/hexanes to give BOC-(2-isobutyl)-3-hydroxypropyl glycine benzyl ester.

B. BOC-(2-isobutyl)-3-hydroxypropyl glycine benzyl ester (0.17 g, 0.45 mmol) is dissolved in pyridine (2 ml), cooled to 0° C., and p-toluenesulfonyl chloride (0.25 g, 1.31 mmol) is added. The mixture is then stirred at room temperature for 16 hours, diluted with ether, and the organic layer washed with 1N HCl, 10% copper sulfate solution, brine. The organic layer is dried over magnesium sulfate, filtered, concentrated in vacuo to give the tosylated product. The primary tosylate (0.23 g, 0.43 mmol) is dissolved in DMF/water (10:1) (2 ml) and sodium azide (0.29 g, 4.46 mmol) is added. The mixture is heated at 90° C. for four hours, cooled, diluted with ether and poured into brine. The organic layer is washed with water, brine, dried over magnesium sulfate, filtered, and concentrated in vacuo. The crude product is purified by flash chromatography, eluting with 10% ethyl aceate in hexanes to give BOC-(2-isobutyl)-3-azidopropyl glycine benzyl ester.

C. Using essentially the procedure of Example 20C, 9-guanidinononanoyl-L-aspartyl-(R,S)-α-isobutylornithine is prepared from BOC-(2-isobutyl)-3-azidopropyl glycine benzyl ester, and isolated as the ditrifluoroacetate salt, M.S., Cal'd: 501, Found: 501.

EXAMPLE 22

6-Guanidinohexanoyl-N-ethyl-glycyl-L-aspartyl-2,2-diethylglycine

A. Using essentially the procedure of Example 20B, BOC-2,2-diethyl glycine benzyl ester is prepared from BOC-2,2-diethylglycine.

B. Using essentially the procedures of Examples 2, 8, 16, and 20, BOC-2,2-diethyl glycine benzyl ester is coupled (EDC) to N-BOC-L-aspartic acid-β-benzyl ester, to N-BOC-N-ethyl glycine (BOP-Cl), and finally to 6-nitro guanidinohexanoic acid to give, after hydrogenation and deprotection as described above, 6-guanidinohexanoyl-N-ethyl-glycyl-L-aspartyl-2,2-diethylglycine, which is isolated as the acetate salt.

EXAMPLE 23

9-Guanidinononanoyl-L-aspartyl-(S)-α-benzyl arginine methyl ester

A. (S)-(2-benzyl)-allylglycine (prepared according to the method of Zydowski, et al., *J. Org. Chem.* 1990, 55, 5437) is protected (di-t-butyldicarbonate, sodium carbonate, THF/water, 7 days) and esterified (methyl iodide, DMF, sodium carbonate, 2 days)to give (S)-BOC-(2-benzyl)allyl glycine methyl ester.

B. Using essentially the procedure of Example 21 A, (S)-BOC-(2-benzyl)allyl glycine methyl ester is converted to (S)-BOC-(2-benzyl)-3-azidopropyl glycine methyl ester.

C. (S)-BOC-(2-benzyl)-3-azidopropyl glycine methyl ester (0.19 g, 0.52 mmol) is dissolved in methanol/chloroform (15:1) (8 ml) and hydrogenated at atmospheric pressure over 10% palladium on carbon for 5 hours. The mixture is filtered, concentrated in vacuo, and the residue triturated with ether/benzene and reconcentrated to give (S)-BOC-(2-benzyl)-ornithine methyl ester hydrochloride.

D. (S)-BOC-(2-benzyl)-ornithine methyl ester hydrochloride (0.2 g, 0.52 mmol) is dissolved in ethanol (10 ml) and triethylamine (0.2 ml, 1.43 mmol) and S-methylisothiourea (0.1 g, 0.74 mmol) are added and the mixture heated at reflux for 16 hours. The solvent is removed in vacuo and the crude product purified by flash chromatography (50% ethyl acetate in hexane) to give (S)-BOC-(2-benzyl)-nitroarginine methyl ester.

E. Using procedures analagous to those described hereinabove, (S)-BOC-(2-benzyl)-nitroarginine methyl ester, is coupled to N-BOC-L-aspartic acid β-benzyl ester and the resulting dipeptide coupled to 9-nitroguanidinononanoic acid. The resulting product is hydrogenated and deprotected to give 9-guanidinononanoyl-L-aspartyl-(S)-α-benzyl arginine methyl ester, which is isolated as the ditrifluoroacetate salt, M.S., Cal'd: 591, Found: 591.

EXAMPLE 24

9-Guanidino-L-aspartyl-(S)-α-isobutylarginine methyl ester

A. Using essentially the procedure of Example 23, Step D, (S)-BOC-(2-isobutyl)-nitroarginine methyl ester is prepared from L-leucine.

B. Using essentially the procedures of Example 23, Step E, 9-guanidino-L-aspartyl-(S)-α-isobutylarginine methyl ester is prepared from (S)-BOC-(2-isobutyl)-nitroarginine methyl ester, and isolated as the ditrifluoroacetate salt, M.S., Cal'd: 557, Found: 557.

EXAMPLE 25

N-(9-guanidinononanoyl-L-aspartyl)-(R)-4-amino-4-isobutylbutyric acid

A. Sodium hydride (2.52 g 60% suspension in mineral oil, washed with hexane, 63.1 mmol) is suspended in THF (200 ml) and cooled to 0° C. under nitrogen. Triethylphosphonoacetate (12.5 ml, 63.1 mmol) is added over 30 minutes and the mixture cooled to −78° C., and BOC-L-leucinal in THF (40 ml) is added over 30 minutes. After stirring at room temperature for 1 hour the excess NaH is quenched by addition of saturated ammonium chloride solution. The mixture is extracted with ethyl acetate and the organic layer washed with satruated sodium bicarbonate solution, brine, then dried over magnesium sulfate, filtered, and concentrated in vacuo. The crude product was purifed by flash chromatography, eluting with 10% ethyl acetate in hexanes to give the corresponding BOC-L-leucine-α,β-unsaturated ethyl ester. The ester (1.5 g, 5.26 mmol) is dissolved in ethanol (20 ml) and hydrogenated at atmospheric pressure over 10% palladium on carbon (0.16 g)

for 24 hours. The mixture is concentrated in vacuo, diluted with ether, filtered, and the filtrate dried over magnesium sulfate, filtered, and concentrated in vacuo to give (R)-BOC-4-amino-4-isobutylbutyric acid ethyl ester.

B. (R)-BOC-4-amino-4-isobutylbutyric acid ethyl ester is coupled sequentially to N-BOC-L-aspartic acid-β-benzyl ester, and to 9-guanidinononanoyl as using procedures described hereinabove. The resulting pseudotripeptide ethyl ester (0.16 g, 0.25 mmol) is dissolved in methanol/water (2:1)(6 ml), cesium carbonate (0.33 g, 1.01 mmol) is added, and the mixture stirred at room temperature for 18 hours. The solvent is removed in-vacuo and the residue dissolved in ethyl acetate. The ethyl acetate is stirred with 1N HCl, then the organic layer is washed with brine, dried over magnesium sulfate, filtered, and concentrated in vacuo. This product was deprotected under hydrogenation conditions as described hereinabove to give N-(9-guanidinononanoyl-L-aspartyl)-(R)-4-amino-4-isobutylbutyric acid, as the trifluroacetate salt, M.S., Cal'd: 472, Found: 472.

EXAMPLE 26

N-[N-(9-Guanidinononanoyl-L-aspartyl)-(R)-4-amino-4-isobutylbutyryl]-L-arginine (R)-BOC-4-amino-4-isobutylbutyric acid ethyl ester is treated with sodium hydroxide in ethanol, followed by acidification to prepare (R)-BOC-4-amino-4-isobutylbutyric acid which is coupled, using essentially the procedure of Example 2, to $N^G$-nitro-L-arginine-benzyl ester p-tosylate, to give the corresponding dipeptide which is, in turn, sequentially coupled to N-BOC-L-aspartic acid-β-benzyl ester and 9-guanidinononanoic acid, then deprotected as described hereinabove to give N-[N-(9-Guanidinononanoyl-L-aspartyl)-(R)-4-amino-4-isobutylbutyryl]-L-arginine, as the ditrifluoroacetate salt, M.S., Cal'd: 628, Found: 628.

EXAMPLE 27

N-[N-(9-Guanidinononanoyl-L-aspartyl)-3-(R)-sec-butyl-3-aminobutyryl]-L-arginine Using essentially the procedures of Examples 25 and 26, the desired product is prepared from BOC-D-isoleucinal, and isolated as the ditrifluoroacetate salt, M.S., Cal'd: 628, Found: 628.

EXAMPLE 28

(R)-4-[N-(9-Guanidinononanoyl-L-aspartyl)-amino]-4-isobutylbutylguanidine

A. (R)-BOC-4-amino-4-isobutylbutyric acid ethyl ester (0.84 g, 2.92 mmol) is dissolved in THF (5 ml) and lithium chloride (0.27 g, 6.3 mmol) and sodium borohydride (0.23 g, 6.3 mmol) and ethanol (9 ml) are added. The mixture is stirred at room temperature for 16 hours, the mixture is cooled to 0° C., and 10% aqueous citric acid solution is added. The mixture is concentrated in vacuo and the residue partitioned between ethyl acetate and water. The organic solution is washed with saturated sodium bicarbonate solution, brine, dried over magnesium sulfate, filtered, and concentrated in vacuo. The crude product is purified by flash chromatography, eluting with 20% ethyl acetate/hexane, to give (R)-BOC-4-amino-4-isobutylbutanol.

B. Using essentially the procedures of Examples 21 and 23 (mesylation, azide displacement, reduction, and nitroguanylation), (R)-BOC-4-amino-4-isobutylbutanol, is converted to (R)-BOC-N-(4-amino-4-isobutylbutyl)-nitroguanidine.

C. Subsequent coupling and deprotection as described hereinabove converts (R)-BOC-N-(4-amino-4-isobutylbutyl)nitroguanidine to (R)-4-[N-(9-guanidinononanoyl-L-aspartyl)-amino]-4-isobutylbutyl-guanidine, which is isolated as the ditrifluoroacetate salt, M.S., Cal'd: 479, Found: 479.

EXAMPLE 29

6-Guanidinohexanoyl-N-ethylglycyl-L-aspartyl-((R)-4-amino-4-isobutylbutyl)guanidine Using procedures analagous to those described hereinabove, the desired product is prepared from (R)-BOC-N-(4-amino-4-isobutylbutyl)nitroguanidine, and isolated as the acetate salt, M.S., Cal'd: 542, Found: 542.

EXAMPLE 30

9-Guanidinononanoyl-L-aspartyl-((S)-4-amino-4-sec-butylbutyl)guanidine

A. Using essentially the procedures of Example 28, (S)-BOC-N-(4-amino-4-sec-butylbutyl)nitroguanidine, is prepared from (S)-BOC-4-amino-4-sec-butylbutyric acid ethyl ester.

B. The desired product is prepared from (S)-BOC-N-(4-amino-4-sec-butylbutyl)nitroguanidine, using sequential coupling and deprotection procedures as described hereinabove, and isolated as the ditrifluoroacetate salt, M.S., Cal'd: 499, Found: 499.

EXAMPLE 31

9-Guanidinononanoyl-L-aspartyl-(R)-6-amino-6-sec-butylhexanoyl-L-arginine

A. Using essentially the procedure of Example 25, Step A, (R)-BOC-6-amino-6-sec-butylhexanoic acid ethyl ester is prepared from BOC-L-isoleucinal and triethyl-4-phosphonocrotonate.

B. Using essentially the procedures of Example 26, the desired product is prepared from (R)-BOC-6-amino-6-sec-butylhexanoic acid ethyl ester, and isolated as the ditrifluoroacetate salt, M.S., Cal'd: 656, Found: 656.

EXAMPLE 32

9-Guanidinononanoyl-L-aspartyl-((R)-6-amino-6-sec-butylhexyl)guanidine

A. Using essentially the procedures of Example 28, (R)-BOC-(6-amino-6-sec-butylhexyl)nitroarginine is prepared from (R)-BOC-6-amino-6-sec-butylhexanoic acid ethyl ester.

B. Using essentially the procedures of Example 28, the desired product is prepared from (R)-BOC-(6-amino-6-sec-butylhexyl)nitroarginine, and isolated as the ditrifluoroacetate salt, M.S., Cal'd: 527, Found: 527.

Compounds within the scope of the present invention inhibit platelet aggregation by inhibiting fibrinogen binding to activated platelets and other adhesive glycoproteins involved in platelet aggregation and blood clotting and are useful in the prevention and treatment of thrombosis associated with certain disease states, such as myocardial infarction, stroke, peripheral arterial disease and disseminated intravascular coagulation in humans and other mammals.

Compounds within the scope of the present invention exhibit activities which interfere with adhesive interactions between abnormal cells and the extracellular matrix and, therefore, are believed to be useful in the treatment of disease conditions, in humans and other animals, characterized by abnormal cell proliferation which have been shown to be dependent on such adhesive interactions (see, for example, *Journ. of Biol. Chem.* 262 (36), 17703–17711 (1987); *Science* 233, 467–470 (1986); and *Cell* 57, 59–69 (1989)).

The compounds of this invention can normally be administered orally or parenterally, in the treatment or prevention of thrombosis associated disease states.

The compounds of this invention may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of platelet aggregation and thrombus inhibiting compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, they are suitably buffered, they are made isotonic with sufficient saline or glucose and sterilized by heating or microfiltration.

The dosage regimen in carrying out the method of this invention is that which insures maximum therapeutic response until improvement is obtained and thereafter the minimum effective level which gives relief. In general, the oral dose may be between about 1 mg/kg and about 200 mg/kg, preferably between about 2 mg/kg to 100 mg/kg, and most preferably between about 10 mg/kg and 100 mg/kg, and the i.v. dose about 0.1 mg/kg to about 20 mg/kg, preferably between about 0.5 mg/kg to 10 mg/kg, bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

The following pharmacologic tests evaluate the inhibitory activity of compounds of the present invention on fibrinogen-mediated platelet aggregation and fibrinogen binding to thrombin-stimulated platelets, and results of these tests correlate to the in-vivo inhibitory properties of compounds of the present invention.

The Platelet Aggregation Assay is based on that described in *Blood* 66 (4), 946–952 (1985). The Fibrinogen-Binding Assay is essentially that of Ruggeri, Z. M., et al., *Proc. Natl. Acad. Sci. USA* 83, 5708–5712 (1986) and Plow, E. F., et al., *Proc. Natl. Acad. Sci., USA* 82, 8057–8061 (1985).

PLATELET AGGREGATION ASSAY

Preparation of Fixed-Activated Platelets

Platelets are isolated from human platelet concentrates using the gel-filtration technique as described by Marguerie, G. A., et al., *J. Biol. Chem.* 254, 5357–5363 (1979) and Ruggeri, Z. M., et al., *J. Clin. Invest.* 72, 1–12 (1983). The platelets are suspended at a concentration of $2 \times 10^8$ cells/ml in a modified calcium-free Tyrode's buffer containing 127 mM sodium chloride, 2 mM magnesium chloride, 0.42 mM $Na_2HPO_4$, 11.9 mM $NaHCO_3$, 2.9 mM KCl, 5.5 mM glucose, 10 mM HEPES, at a pH of 7.35 and 0.35% human serum albumin (HSA). These washed platelets are activated by addition of human α-thrombin at a final concentration of 2 units/ml, followed by thrombin inhibitor I-2581 at a final concentration of 40 μM. To the activated platelets is added paraformaldehyde to a final concentration of 0.50% and this incubated at room temperature for 30 minutes. The fixed activated platelets are then collected by centrifugation at $650 \times g$ for 15 minutes. The platelet pellets are washed four times with the above Tyrode's-0.35% HSA buffer and resuspended to $2 \times 10^8$ cells/ml in the same buffer.

Platelet Aggregation Assay

The fixed activated platelets are incubated with a selected dose of the compound to be tested for platelet aggregation inhibition for one minute and aggregation initiated by addition of human fibrinogen to a final concentration of 250 μg/ml. A platelet aggregation profiler Model PAP-4 is used to record the platelet aggregation. The extent of inhibition of aggregation is expressed as the percentage of the rate of aggregation observed in the absence of inhibitor. $IC_{50}$, i.e., the amount of inhibitor required to reduce the aggregation rate by 50%, is then calculated for each compound (see, for example, Plow, E. F., et al., *Proc. Natl. Acad. Sci., USA* 82, 8057–8061 (1985)).

FIBRINOGEN-BINDING ASSAY

Platelets are washed free of plasma constituents by the albumin density-gradient technique of Walsh, P. N., et al., *Br. J. Haematol.* 281–296 (1977), as modified by Trapani-Lombardo, V., et al., *J. Clin Invest.* 76, 1950–1958 (1985). In each experimental mixture platelets in modified Tyrode's buffer (Ruggeri, Z. M., et al., *J. Clin. Invest.* 72, 1–12 (1983)) are stimulated with human α-thrombin at 22°–25° C. for 10 minutes ($3.125 \times 10^{11}$ platelets per liter and thrombin at 0.1 NIH units/ml). Hirudin is then added at a 25-fold excess (unit/unit) for 5 minutes before addition of the $^{125}$Iabeled fibrinogen and the compound to be tested. After these additions, the final platelet count in the mixture is $1 \times 10^{11}$/liter. After incubation for an additional 30 minutes at 22°–25° C., bound and free ligand are separated by centrifuging 50 μl of the mixture through 300 μl of 20% sucrose at 12,000×g for 4 minutes. The platelet pellet is then separated from the rest of the mixture to determine platelet-bound radioactivity. Nonspecific binding is measured in mixtures containing an excess of unlabeled ligand. When binding curves are analyzed by Scatchard analysis, nonspecific binding is derived as a fitted parameter from the binding isotherm by means of a computerized program (Munson, P. J., *Methods Enzymol.* 92, 542–576 (1983)). To determine the concentration of each inhibitory compound necessary to inhibit 50% of fibrinogen binding to thrombin-stimulated platelets ($IC_{50}$), each compound is tested at 6 or more concentrations with $^{125}$labeled fibrinogen held at 0.176 μmol/liter (60 μg/ml). The $IC_{50}$ is derived by plotting residual fibrinogen binding against the logarithm of the sample compound's concentration.

Compounds of the present invention exhibit marked activity in the foregoing tests and are considered useful in the prevention and treatment of thrombosis associated with certain disease states. Results of testing of compounds of the present invention by the above methods are presented in the Table I below.

The compounds listed in Table I are prepared by the methods described herein, by analogous methods, or by methods known in the art. Mass spectral analysis, where provided, is by Low Resolution Fast Atom Bombardment with the "calculated" values being $(M+1)^+$.

TABLE I

| | Inhibition of $^{125}$I-Fibrinogen Binding to Platelets | Inhibition of Fibrinogen Mediated Platelet Aggregation | |
|---|---|---|---|
| | $IC_{50}$ (μM) | $IC_{50}$ (μM) | % inhibition at |
| | | | 100 μM |
| L-arginyl-L-aspartyl-L-valine M.S., Cal'd: 389, Found: 389 | >200 | 100 | 49 |
| L-arginylglycyl-L-aspartyl-α-isobutylamide ditrifluoroacetate, m.p. 90–95° C. | 26.5 | 3.6 | 89 |
| L-ornithylglycyl-L-aspartyl-L-valine ditrifluoroacetate, m.p. 122–125° C., M.S., Cal'd: 632, Found: 632 | Inhibited <50% at 50 μg/ml | 15 | 80 |
| L-arginylglycyl-L-aspartic acid α-benzyl ester ditrifluoroacetate, m.p. 85–87° C. | 25.0 | 14 | 96 |
| L-arginylsarcosyl-L-aspartyl-L-valine ditrifluoroacetate, m.p. 145° C. (dec), M.S., Cal'd: 460, Found: 460 | 14 | 14 | 92 |
| L-arginylglycyl-L-aspartyl-L-(N-methyl)-valine ditrifluoroacetate, m.p. 153° C. (dec) | Inhibited <50% at 50 μg/ml | 160 | 30 |
| L-arginylglycyl-L-aspartyl glycine ditrifluoroacetate, m.p. 85–90° C., M.S., Cal'd: 404, Found: 404 | — | 14.3 | 91 |
| N-(L-arginyl-2-aminoethyl)-L-aspartyl-L-valine tritrifluoroacetate, m.p. 91–95° C., M.S., Cal'd: 432, Found: 432 | >200 | — | 10 |
| L-arginyl-glycyl-L-N-methylaspartyl-L-valine ditrifluoroacetate, M.S., Cal'd: 460, Found: 460 | — | >64 | — |
| N-(5-Aminopentanoyl) glycyl-L-aspartyl-L-valine trifluoroacetate, m.p. 95–99° C. | 68.5 | >64 | 67 |
| N-δ-(L-arginyl)-L-ornithyl-L-valine tritrifluoroacetate, M.S., Cal'd: 373, Found: 373 | — | >100 | 20 |
| L-arginyl-L-aspartyl-L-valine ditrifluoroacetate, m.p. 90–95° C., M.S., Cal'd: 389, Found: 389 | >200 | 100 | 49 |
| L-arginyl glycyl glycyl-L-valine ditrifluoroacetate, M.S., Cal'd: 388, Found: 388 | >200 | >100 | 10 |
| L-arginyl glycyl-L-aspartic acid α-benzyl ester ditrifluoroacetate, M.S., Cal'd: 437, Found: 437 | 25.0 | 14 | 96 |
| L-ornithyl-glycyl-L-aspartyl-L-valine ditrifluoroacetate, m.p. 122–125° C. | Inhibited <50% at 50 μg/ml | 15 | 80 |
| N-(5-guanidinopentanoyl)glycyl-L-aspartyl-L-valine dihydrochloride, m.p. 60–70° C. | 0.7 | 2.3 | 92 |
| L-arginyl-sarcosyl-L-aspartyl-L-valine ditrifluoroacetate, m.p. 145° C. (dec) | 14 | 14 | 92 |
| L-arginylglycyl-L-alanyl-L-valine ditrifluoroacetate, M.S., Cal'd: 402, Found: 402 | Inhibited <50% at 50 μg/ml | >100 | 17.5 |
| L-arginylglycyl-L-aspartyl-L-(N-methyl)-valine ditrifluoroacetate, M.S., Cal'd: 460, Found: 460 | Inhibited <50% at 50 μg/ml | 160 | 30 |
| 2-[N-(5-guanidinopentanoyl)glycyl-L-aspartyl]-1,2,3,4-tetrahydroisoquinoline, M.S., Cal'd: 447, Found: 447 | 130 | 20.4 | 48 |
| N-(5-guanidinopentanoyl)glycyl-L-aspartylphenethylamide acetate, m.p. 90–100° C. | 20 | 2.1 | 86 |
| | | | 25 μM |
| 5-guanidinovaleroyl-L-aspartyl-L-valine trifluoroacetate, M.S., Cal'd: 374, Found: 374 | — | — | 28 |
| 9-aminononanoyl-L-aspartyl-L-valine trifluoroacetate, M.S., Cal'd: 388, Found: 388 | 30 | 19.1 | 10.1 |
| 9-guanidinononanoyl-L-aspartyl-L-valine trifluoroacetate, M.S., Cal'd: 430, Found: 430 | 0.2 | 1.7 | 96 |
| 11-guanidinoundecanoyl-L-aspartyl-L-valine trifluoroacetate, M.S., Cal'd: 458, Found: 458 | 17 | — | 36 |
| 9-guanidinononanoyl-L-aspartyl-L-leucine, | 0.4 | 0.59 | 95 |

TABLE I-continued

| | Inhibition of $^{125}$I-Fibrinogen Binding to Platelets | Inhibition of Fibrinogen Mediated Platelet Aggregation | |
|---|---|---|---|
| | IC$_{50}$ ($\mu$M) | IC$_{50}$ ($\mu$M) | % inhibition at |
| M.S., Cal'd: 444, Found: 444 | | | |
| 5-guanidino-N-(ethyl)-glycyl-L-aspartyl-L-arginine ditrifluoroacetate, M.S., Cal'd: 516, Found: 516 | 1.9 | 0.23 | 93 |
| 5-guanidinopentanoyl-N-(ethyl)-glycyl-L-aspartyl-L-leucine trifluoroacetate, M.S., Cal'd: 473, Found: 473 | 0.39 | 0.54 | 90 |
| 6-guanidinohexanoyl-N-ethyl-glycyl-L-aspartyl-L-leucine trifluoroacetate, M.S., Cal'd: 487, Found: 487 | 5.4 | 0.56 | 95.5 |
| 5-(Imidazol-1-yl)-valeroylglycyl-L-aspartyl-L-valine, M.S., Cal'd: 440, Found: 440 | 1.25 | 20.2 | 58 |
| 5-(Imidazol-1-yl)-pentanoyl-sarcosyl-L-aspartyl-L-valine trifluoroacetate, M.S., Cal'd: 454, Found: 454 | 0.15 | 1.5 | 95 |
| 6-(Imidazol-1-yl)-hexanoyl-glycyl-L-aspartyl L-valine trifluoroacetate, M.S., Cal'd: 454, Found: 454 | 2.8 | 17.0 | 67 |
| 6-(Imidazol-1-yl)-hexanoylsarcosyl-L-aspartyl, M.S., Cal'd: 468, Found: 468 | 1.25 | 2.8 | 94 |
| 6-(Imidazol-1-yl)-hexanoyl-N-ethylglycyl-L-aspartyl-L-valine trifluoroacetate, M.S., Cal'd: 482, Found: 482 | 0.90 | 1.0 | 95 |
| 8-(Imidazol-1-yl)-octanoyl-L-aspartyl-L-valine trifluoroacetate, M.S., Cal'd: 425, Found: 425 | 0.86 | 11.6 | 78 |
| 9-(Imidazol-1-yl)-nonanoyl-L-aspartyl-L-valine, M.S., Cal'd: 439, Found: 439 | .50 | 3.4 | 96 |
| 9-guanidinononanoyl-L-aspartyl-L-arginine isobutyl ester, M.S., Cal'd: 543, Found: 543 | 0.625 | 0.54 | 97.0 |
| 8-Guanidinooctanoyl-L-aspartic acid-$\alpha$-isobutylamide trifluoroacetate, M.S., Cal'd: 372, Found: 372 | 14.5 | 7.8 | 81 |
| 12-Guanidinododecanoyl-L-aspartyl-L-valine trifluoroacetate, M.S., Cal'd: 472, Found: 472 | 7.0 | — | 36 |
| 9-Guanidinononanoyl-L-aspartyl-L-isoleucine-trifluoroacetate, M.S., Cal'd: 444, Found: 444 | 0.38 | 4.2 | 93 |
| 9-Guanidinononanoyl-L-aspartyl-L-arginine-ditrifluoroacetate, M.S., Cal'd: 487, Found: 487 | 0.13 | 0.26 | 97 |
| 8-Guanidinooct-2-enoyl-L-aspartyl-L-arginine ditrifluoroacetate, M.S., Cal'd: 471, Found: 471 | 0.58 | 0.63 | 90 |
| 8-Guanidinooctanoyl-L-aspartyl-arginine ditrifluoroacetate, M.S., Cal'd: 473, Found: 473 | 0.33 | 2.2 | 94 |
| 10-Guanidinodec-2-enoyl-L-aspartyl-L-valine trifluoroacetate, M.S., Cal'd: 442, Found: 442 | 12.0 | 8.8 | 77 |
| 9-Guanidinononanoyl-L-aspartyl-arginyl-isoleucine ditrifluoroacetate, M.S., Cal'd: 600, Found: 600 | 1.2 | 2.4 | 93 |
| 9-Guanidinononanoyl-L-aspartyl-isoleucyl-arginine ditrifluoroacetate, M.S., Cal'd: 600, Found: 600 | 0.37 | 0.67 | 94 |
| 8-Guanidinooctanoyl-L-aspartyl-L-valine trifluoroacetate, M.S., Cal'd: 415, Found: 415 | 2.8 | 2.7 | 89 |
| 8-Guanidinooct-2-enoyl-L-aspartyl-L-valine trifluoroacetate, M.S., Cal'd: 414, Found: 414 | 0.84 | 0.29 | 96 |
| 8-Guanidino-2-(R,S)-ethyl-octanoyl-L-aspartyl-L-valine trifluoroacetate, M.S., Cal'd: 444, Found: 444 | >200 | — | 30 |
| 10-Guanidinodecanoyl-L-aspartyl-L-valine trifluoroacetate, M.S., Cal'd: 444, Found: 444 | 2.5 | 10.3 | 77 |
| 9-Guanidinonon-2-(E)-enoyl-L-aspartyl-L-valine trifluoroacetate, M.S., Cal'd: 428, Found: 428 | 0.43 | — | 24 |
| 11-Guanidino-undecanoyl-L-aspartyl-L-valine trifluoroacetate, M.S., Cal'd: 458, Found: 458 | 17.0 | — | 36 |
| 4-Guanidinobutanoyl-glycyl-L-aspartyl-L-valine trifluoroacetate, m.p. 50–52° C., M.S., Cal'd: 417, Found: 417 | 10.0 | 21.9 | 43 |
| 5-Guanidinovaleroyl-sarcosyl-L-aspartyl-L-valine trifluoroacetate, M.S., Cal'd: 445, Found: 445 | 1.0 | 0.52 | 94 |
| 6-Guanidinohexanoyl-glycyl-L-aspartyl-L-valine trifluoroacetate, M.S., Cal'd: 445, Found: 445 | 1.4 | 6.5 | 90 |
| 4-Guanidinobutanoyl-L-sarcosyl-L-aspartyl-L-valine trifluoroacetate, m.p. 62–64° C., M.S., Cal'd: 431, Found: 431 | 3.3 | 10.8 | 84 |
| 6-Guanidinohexanoyl-L-sarcosyl-L-aspartyl-L-valine trifluoroacetate, m.p. 65–70° C., M.S., Cal'd: 459, Found: 459 | 0.32 | 0.63 | 97 |
| 4-Guanidinobutanoyl-L-$\beta$-alanyl-L-aspartyl-L-valine trifluoroacetate, M.S., Cal'd: 431, Found: 431 | 10.0 | 10.6 | 78 |
| 7-Guanidinoheptanoyl-glycyl-L-aspartyl-L-valine trifluoroacetate, M.S., Cal'd: 459, Found: 459 | 6.4 | 21.0 | 56 |

TABLE I-continued

| | Inhibition of $^{125}$I-Fibrinogen Binding to Platelets | Inhibition of Fibrinogen Mediated Platelet Aggregation | |
|---|---|---|---|
| | IC$_{50}$ ($\mu$M) | IC$_{50}$ ($\mu$M) | % inhibition at |
| 7-Guanidinoheptanoyl-L-sarcosyl-L-aspartyl-L-valine trifluoroacetate, M.S., Cal'd: 473, Found: 473 | 5.1 | — | 14 |
| 6-Guanidinohexanoyl-L-sarcosyl-L-aspartyl-L-leucine trifluoroacetate, M.S., Cal'd: 473, Found: 473 | 0.09 | 0.33 | 88 |
| 6-Guanidinohexanoyl-N-benzylglycyl-L-aspartyl-L-valine trifluoroacetate, M.S., Cal'd: 535, Found: 535 | 0.84 | 5.7 | 85 |
| 6-Guanidinohexanoyl-N-ethylglycine-L-aspartyl-L-valine trifluoroacetate, M.S., Cal'd: 473, Found: 473 | 0.12 | 0.38 | 96 |
| 6-Guanidinohexanoyl-N-isobutylglycyl-L-aspartyl-L-valine trifluoroacetate, M.S., Cal'd: 501, Found: 501 | 0.10 | 1.5 | 86 |
| 6-Guanidinohexanoyl-N-(2-methylpentyl)glycine-L-aspartic acid-L-valine trifluoroacetate, M.S., Cal'd: 529, Found: 529 | >200 | 10.5 | 86 |
| 6-Guanidinohexanoyl-N-ethylglycyl-L-aspartyl-L-phenylalanine trifluoroacetate, M.S., Cal'd: 521, Found: 521 | 0.20 | 1.3 | 97 |
| 6-Guanidinohexanoyl-N-ethylglycyl-L-aspartyl-L-isoleucine trifluoroacetate, M.S., Cal'd: 487, Found: 487 | 0.05 | 0.56 | 96 |
| 6-Guanidinohexanoyl-N-(2-propyl)glycyl-L-aspartyl-L-valine trifluoroacetate, M.S., Cal'd: 487, Found: 487 | 1.1 | 8.6 | 83 |
| 6-Guanidinohexanoyl-N-ethylglycyl-L-aspartyl-L-arginine ditrifluoroacetate, M.S., Cal'd: 530, Found: 530 | 0.24 | 1.4 | 97 |
| 5-Guanidinopentanoyl-N-ethylglycyl-L-aspartyl-L-valine trifluoroacetate, M.S., Cal'd: 447, Found: 447 | 0.04 | 0.63 | 91 |
| 6-Guanidinohexanoyl-sarcosyl-L-aspartyl-L-arginine ditrifluoroacetate, M.S., Cal'd: 516, Found: 516 | 0.52 | 2.1 | 97 |
| 6-Aminohexanoyl-N-ethylglycyl-L-aspartyl-L-valine ditrifluoroacetate, M.S., Cal'd: 431, Found: 431 | 4.0 | 4.1 | 92 |
| 6-Guanidinohexanoyl-N-isopropylglycyl-L-aspartyl-L-valine, M.S., Cal'd: 487, Found: 487 | 1.1 | 8.6 | 83 |
| 9-Guanidinononanoyl-L-aspartyl-L-arginine isobutyl amide ditrifluoroacetate, M.S., Cal'd: 542, Found: 542 | 3.0 | 2.20 | 89 |
| 8-Guanidinooctanoyl-L-aspartyl-L-lysine bis(trifluoroacetate) salt, M.S., Cal'd: 445, Found: 445 | 0.78 | 1.6 | 93 |
| 9-(Imidazol-2-methyl-1-yl)nonanoyl-L-aspartyl-L-aspartyl-L-valine trifluoroacetate, M.S., Cal'd: 453, Found: 453 | 80 | 3.0 | 74 |
| 9-Guanidinononanoyl-L-aspartyl-L-arginine isobutyl amide ditrifluoroacetate, M.S., Cal'd: 542, Found: 542 | 3.0 | 2.20 | 89 |
| 8-Guanidinooctanoyl-L-aspartyl-L-lysine bis(trifluoroacetate) salt, M.S., Cal'd: 445, Found: 445 | 0.78 | 1.6 | 93 |
| 8-Guanidinooctanoyl-L-aspartyl-L-valine-5-tetrazole, M.S., Cal'd: 440, Found: 440 | — | >25 | 32 |
| 10-(Imidazol-1-yl)decanoyl-L-aspartyl-L-valine trifluoroacetate, M.S., Cal'd: 453, Found: 453 | 20 | >25 | 45.0 |
| 9-Guanidinononanoyl-L-aspartyl-$\beta$-alanyl-L-arginine ditrifluoroacetate, M.S., Cal'd: 558, Found: 558 | 0.64 | 1.5 | 93.0 |
| 9-Guanidinononanoyl-L-aspartyl-glycyl-L-arginine ditrifluoroacetate, M.S., Cal'd: 544, Found: 544 | 7.0 | 2.2 | 85.0 |
| 8-Guanidinooctanoyl-glycyl-glycine trifluoroacetate, M.S., Cal'd: 316, Found: 316 | — | — | 12 |
| 7-(Imidazol-1-yl)heptanoyl-L-aspartyl-L-valine trifluoroacetate, M.S., Cal'd: 411, Found: 411 | 2.0 | >25 | 35 |
| 6-(2-Methylimidazol-1-yl)hexanoyl-N-(ethyl)-glycyl-L-aspartyl-L-valine trifluoroacetate, M.S., Cal'd: 496, Found: 496 | 0.35 | 1.9 | 93.0 |
| 4-Guanidinobutanoyl-N-(ethyl)glycyl-L-aspartyl-L-valine trifluoroacetate, M.S., Cal'd: 445, Found: 445 | 0.45 | 2.7 | 94 |
| 7-(Imidazol-1-yl)heptanoyl-N-(ethyl)glycyl-L-aspartyl-L-valine trifluoroacetate, M.S., | 1.3 | 10.8 | 82 |

TABLE I-continued

| | Inhibition of $^{125}$I-Fibrinogen Binding to Platelets | Inhibition of Fibrinogen Mediated Platelet Aggregation | |
|---|---|---|---|
| | IC$_{50}$ ($\mu$M) | IC$_{50}$ ($\mu$M) | % inhibition at |
| Cal'd: 496, Found: 496 | | | |
| 6-Guanidinohexanoyl-sarcosyl-L-aspartic acid-$\beta$-methylester-L-valine methylester trifluoroacetate, M.S., Cal'd: 487, Found: 487 | — | — | — |
| 9-Guanidinononanoyl-L-aspartyl-isoleucine-4-guanidinobutyl amide ditrifluoroacetate, M.S., Cal'd: 556, Found: 556 | 0.24 | 5.7 | 95.0 |
| 6-Guanidinohexanoyl-sarcosyl-L-aspartic acid-$\beta$-methylester-L-valine trifluoroacetate, M.S., Cal'd: 587, Found: 587 | — | — | — |
| 6-Guanidinohexanoyl-N-(ethyl)glycyl-L-aspartyl-L-tyrosine trifluoroacetate, M.S., Cal'd: 537, Found: 537 | 0.18 | 1.25 | 95 |
| 6-Guanidinohexanoyl-N-cyclopentylglycine-L-aspartyl-L-valine trifluoroacetate, M.S., Cal'd: 513, Found: 513 | 0.88 | 5.7 | 76.0 |
| 9-Guanidinononanoyl-L-aspartyl-(des-carboxy)-L-arginine ditrifluoroacetate, M.S., Cal'd: 443, Found: 443 | 0.52 | 4.4 | 84 |
| 8-Guanidinooctanoyl-L-aspartyl-(des-carboxy)-L-arginine ditrifluoroacetate, M.S., Cal'd: 429, Found: 429 | 0.99 | 1.9 | 91 |
| 6-Guanidinohexanoyl-sarcosyl-L-aspartyl-L-lysine ditrifluoroacetate, M.S., Cal'd: 488, Found: 488 | 0.34 | 4.1 | 86.0 |
| 6-Guanidinohexanoyl-sarcosyl-L-aspartyl-L-tyrosine trifluoroacetate, M.S., Cal'd: 523, Found: 523 | 3.6 | 7.3 | 94.0 |
| 6-Guanidinohexanoyl-sarcosyl-L-aspartyl-L-tryptophan ditrifluoroacetate, M.S., Cal'd: 546, Found: 546 | 0.19 | 6.6 | 89.0 |
| 6-(2-Phenylimidazol-1-yl)hexanoyl-sarcosyl-L-aspartyl-L-valine trifluoroacetate, M.S., Cal'd: 544, Found: 544 | 0.38 | 5.6 | 84.0 |
| 6-(2-Ethylimidazol-1-yl)hexanoyl-sarcosyl-L-aspartyl-L-valine trifluoroacetate, M.S., Cal'd: 496, Found: 496 | 0.313 | 4.9 | 89.0 |
| 6-Guanidinohexanoyl-N-(ethyl)glycyl-L-aspartyl-L-tryptophan ditrifluoroacetate, M.S., Cal'd: 560, Found: 560 | 0.13 | 1.3 | 91.0 |
| 9-Guanidinononanoyl-L-aspartyl-$\delta$-aminobutyryl-L-arginine ditrifluoroacetate, M.S., Cal'd: 572, Found: 572 | 1.6 | 24.0 | 56.0 |
| 9-Guanidinononanoyl-L-aspartyl-$\beta$-alanyl-L-isoleucine trifluoroacetate, M.S., Cal'd: 515, Found: 515 | 54 | 999 | 9.0 |
| 9-Guanidinononanoyl-L-aspartyl-glycyl-L-isoleucine trifluoroacetate, M.S., Cal'd: 501, Found: 501 | 40 | 25.0 | 54.0 |
| 9-Guanidinononanoyl-L-aspartyl-L-norleucyl-L-arginine ditrifluoroacetate, M.S., Cal'd: 600, Found: 600 | 0.21 | 0.3 | 95.0 |
| 9-Guanidinononanoyl-L-aspartyl-$\alpha$-benzylphenyl-alanine trifluoroacetic acid salt, M.S., Cal'd: 568, Found: 568 | >200 | >25 | 10.0 |
| 9-Guanidinononanoyl-L-aspartyl-homo-L-isoleucyl-L-arginine ditrifluoroacetate, M.S., Cal'd: 614, Found: 614 | 1.25 | 1.9 | 94.0 |
| 9-Guanidinononanoyl-L-aspartyl-D-isoleucyl-L-arginine ditrifluoroacetate, M.S., Cal'd: 600, Found: 600 | 10.2 | 13.1 | 75.0 |
| 9-Guanidinononanoyl-L-aspartyl-(R,S)-$\alpha$-isobutyl ornithine ditrifluoroacetate, M.S., Cal'd: 501, Found: 501 | — | >25 | 4.0 |
| L-Lysylglycyl-L-aspartyl-L-valine ditrifluoroacetate, M.S., Cal'd: 418, Found: 418 | 60 | >25 | 8.0 |
| 9-Guanidinononanoyl-L-aspartyl-(R)-4-amino-4-isobutylbutyryl-L-arginine ditrifluoroacetate, M.S., Cal'd: 628, Found: 628 | 2.1 | — | — |
| 9-Guanidinononanoyl-L-aspartyl-L-arginyl-L-arginine tritrifluoroacetate, M.S., Cal'd: 643, Found: 643 | 15.0 | 15.0 | 68 |
| 9-Guanidinononanoyl-L-aspartyl-$\alpha,\alpha$-diethyl-glycyl-L-arginine ditrifluoroacetate, M.S., Cal'd: 600, Found: 600 | 40 | >25 | 20.0 |
| 9-Guanidinononanoyl-L-aspartyl-L-arginine-3-methylbutyl ester ditrifluoroacetate, M.S., Cal'd: 557, Found: 557 | 0.15 | 1.7 | 97 |
| 8-Guanidinooctanoyl-L-aspartyl-L-phenyl- | 0.2 | 0.69 | 96 |

TABLE I-continued

| | Inhibition of $^{125}$I-Fibrinogen Binding to Platelets | Inhibition of Fibrinogen Mediated Platelet Aggregation | |
|---|---|---|---|
| | IC$_{50}$ ($\mu$M) | IC$_{50}$ ($\mu$M) | % inhibition at |
| alanine trifluoroacetate, M.S., Cal'd: 464, Found: 464 | | | |
| 9-Guanidinononanoyl-L-aspartyl-L-arginine-2-methyl-butylester ditrifluoroacetate, M.S., Cal'd: 557, Found: 557 | 0.12 | 0.73 | 97 |
| 9-Guanidinononanoyl-L-aspartyl-L-arginine-cyclohexylester ditrifluoroacetate, M.S., Cal'd: 570, Found: 570 | 0.26 | 0.82 | 91.0 |
| 11-Aminoundecanoyl-L-aspartyl-L-valine trifluoroacetate, M.S., Cal'd: 416, Found: 416 | 0.58 | 1.7 | 0.98 |
| N-(9-guanidinononanoyl-L-aspartyl)-(R)-4-amino-4-isobutyl butyric acid ditrifluoroacetate, M.S., Cal'd: 472, Found: 472 | 54 | >25 | 13.0 |
| 4-[N-(9-guanidinononanoyl-L-aspartyl)amino]-4-isobutyl butyl guanidine ditrifluoroacetate, M.S., Cal'd: 479, Found: 479 | 10.5 | 2.0 | 94.0 |
| 8-Aminooctanoyl-sarcosyl-L-aspartyl-L-valine trifluoroacetate, M.S., Cal'd: 445, Found: 445 | 0.23 | 2.6 | 96 |
| 6-Guanidinohexanoyl-sarcosyl-L-aspartyl-L-valine methylester trifluoroacetate, M.S., Cal'd: 473, Found: 473 | — | — | — |
| 5-(5'-Guanidinopentyl-1H-tetrazole-1-acetyl-acetyl-L-aspartyl-L-valine trifluoroacetate salt, M.S., Cal'd: 470, Found: 470 | 2.2 | >25 | 40.0 |
| 9-Guanidinononanoyl-L-aspartyl-$\beta$-homo-L-isoleucyl psi(CH$_2$NH)-L-arginine tritrifluoroacetate, M.S., Cal'd: 586, Found: 586 | >200 | >25 | 38 |
| 9-Guanidinononanoyl-L-aspartyl-L-isoleucyl-D-arginine ditrifluoroacetate, M.S., Cal'd: 600, Found: 600 | 15.0 | 2.0 | 97.0 |
| 9-Guanidinononanoyl-L-aspartyl-(S)-$\alpha$-benzyl-L-arginine methylester ditrifluoroacetate, M.S., Cal'd: 591, Found: 591 | 20 | 13.3 | 69 |
| N-(9-Guanidinononanoyl-L-aspartyl)-3-amino-2-sec-butyl propionic acid L-arginine amide ditrifluoroacetate, M.S., Cal'd: 614, Found: 614 | 4.3 | 0.45 | 89.0 |
| 9-Guanidinononanoyl-L-aspartyl-D-homoisoleucyl-L-arginine ditrifluoroacetate, M.S., Cal'd: 614, Found: 614 | 4.7 | 5.8 | 98 |
| 9-Guanidinononanoyl-L-aspartyl-L-phenylalanine-L-arginine ditrifluoroacetate, M.S., Cal'd: 634, Found: 634 | 6.0 | 0.32 | 98.0 |
| 9-Guanidinononanoyl-L-aspartyl-L-arginine methylester ditrifluoroacetate, M.S., Cal'd: 501, Found: 501 | — | 1.7 | 91.0 |
| 9-Guanidinononanoyl-L-aspartyl-L-isoleucyl-L-isoleucine trifluoroacetate, M.S., Cal'd: 557, Found: 557 | — | >25 | 45.0 |
| 9-Guanidinononanoyl-L-aspartyl-L-alanyl-L-arginine ditrifluoroacetate, M.S., Cal'd: 558, Found: 558 | — | 0.54 | 89.0 |
| 9-Guanidinononanoyl-L-aspartyl-L-t-butylglycyl-L-arginine ditrifluoroacetate. M.S., Cal'd: 600, Found: 600 | — | 1.5 | 96.0 |
| 9-Guanidinononanoyl-L-aspartyl-[(S)-4-amino-4-sec-butyl-butyl]guanidine ditrifluoroacetate, M.S., Cal'd: 499, Found: 499 | — | 11.2 | 76.0 |
| 9-Guanidinononanoyl-L-aspartyl-2-amino-butanoyl-L-arginine ditrifluoroacetate, M.S., Cal'd: 572, Found: 572 | — | 0.36 | 90.0 |
| 9-Guanidinononanoyl-L-aspartyl-D-$\beta$-homoisoleucyl-(des-carboxy)-L-arginine ditrifluoroacetate, M.S., Cal'd: 570, Found: 570 | — | 3.3 | 94.0 |
| 9-Guanidinononanoyl-L-aspartyl-(S)-$\alpha$-isobutyl-arginine methylester ditrifluoroacetate, M.S., Cal'd: 557, Found: 557 | — | >25 | 0.0 |
| 9-Guanidinononanoyl-L-aspartyl-L-valine-L-arginine ditrifluoroacetate, M.S., Cal'd: 586, Found: 586 | — | 0.22 | 98.0 |
| 9-Guanidinononanoyl-L-aspartyl-cyclohexyl-alanyl-L-arginine ditrifluoroacetate, M.S., Cal'd: 640, Found: 640 | — | — | — |
| 9-Guanidinononanoyl-L-aspartyl-L-leucyl-L-arginine ditrifluoroacetate, M.S., Cal'd: 600, Found: 600 | — | 0.52 | 96.0 |
| 9-Guanidinononanoyl-L-aspartyl-(R)-6-amino-6-sec-butyl hexanoyl-L-arginine ditrifluoroacetate, M.S., Cal'd: 656, Found; 656 | — | — | — |
| 6-Guanidinohexanoyl-N-ethylglycyl-L-aspartyl-[(R)- | — | — | — |

TABLE I-continued

| | Inhibition of $^{125}$I-Fibrinogen Binding to Platelets | Inhibition of Fibrinogen Mediated Platelet Aggregation | |
|---|---|---|---|
| | IC$_{50}$ ($\mu$M) | IC$_{50}$ ($\mu$M) | % inhibition at |
| 4-amino-4-isobutyl-butyl]guanidine acetate, M.S., Cal'd: 542, Found: 542 | | | |
| 9-guanidinononanoyl-L-aspartyl-[(R)-6-amino-6-sec-butyl-hexyl]guanidine ditrifluoroacetate, M.S., Cal'd: 527, Found: 527 | — | — | — |
| 9-Guanidinononanoyl-L-aspartyl-norvalyl-L-arginine ditrifluoroacetate, M.S., Cal'd: 585, Found: 585 | — | — | — |
| N-(9-Guanidinononanoyl-L-aspartyl)-3-(R)-sec-butyl-3-aminobutyryl-L-arginine ditrifluoroacetate, M.S., Cal'd: 628, Found: 628 | — | — | — |
| 6-Guanidinohexanoyl-sarcosyl-L-aspartyl-L-valine-butylester trifluoroacetate, M.S., Cal'd: 515, Found: 515 | — | 4.5 | 90.0 |
| 6-Guanidinohexanoyl-sarcosyl-L-aspartyl-L-valine-butylester trifluoroacetate, M.S., Cal'd: 515, Found: 515 | — | 4.5 | 90.0 |
| 9-Guanidinononanoyl-L-aspartyl-D-homo-norleucyl-L-arginine ditrifluoroacetate, M.S., Cal'd: 614, Found: 614 | — | — | — |
| 8-Guanidinooctanoyl L-aspartic acid 8-guanidino-1-aminooctane-$\alpha$-amide ditrifluoroacetate, M.S., Cal'd: 485, Found: 485 | — | — | — |
| 6-Guanidinohexanoyl-sarcosyl-L-aspartyl-$\beta$-butylester-L-valine trifluoroacetate, M.S., Cal'd: 515, Found: 515 | — | >25 | 18.0 |
| 6-Guanidinohexanoyl-sarcosyl-L-aspartyl-$\beta$-butylester-L-valine-butyl ester trifluoroacetate, M.S., Cal'd: 571, Found: 571 | — | — | — |
| 6-Guanidinohexanoyl-N-ethylglycyl-L-aspartyl-2,2-diethyl glycine, M.S., Cal'd: 464, Found: 464 | 5.0 | 11.4 | 73.0 |

One skilled in the art will readily appreciate that the present invention is well adapted to carry out the objects and obtain the ends and advantages mentioned, as well as those inherent therein. The compounds, compositions, and methods described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

We claim:

1. A compound of the formula

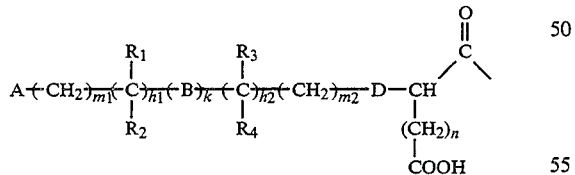

wherein:

A is

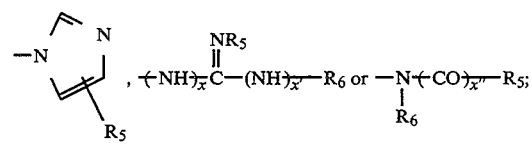

B and D are independently —CH$_2$—NH—, —CH$_2$—S—, —CH$_2$—O—,

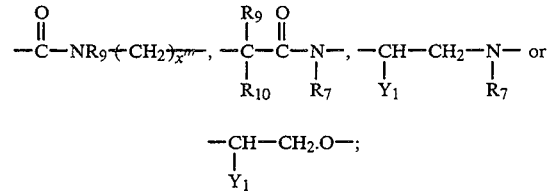

B may also be 5-tetrazol-1-yl or —CR$_7$=CR$_8$—;

Z is —OR$_a$, a D- or L-isomer of an $\alpha$-amino acid bonded at the $\alpha$-nitrogen, a dipeptide bonded at the N-terminal $\alpha$-amino acid, or —NR$_a$R$_x$, where R$_x$ is H or

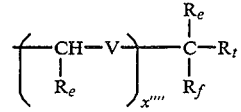

where V is

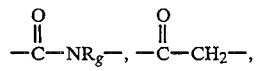

—(CH$_2$)$_p$—, —CH=CH—, —CH$_2$NH—, —CH$_2$—O—, or —CH$_2$—S—;

R$_e$ and R$_f$ are independently H, alkyl, cycloalkyl, cycloalkylmethyl, or —(CH$_2$)$_s$—R$_z$ where R$_z$ is —COOR$_n$, —OR$_n$, —SR$_n$, —NR$_n$, R$_o$,

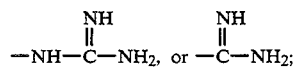

$R_{1-10}$, and $R_n$ are independently H, alkyl, cycloalkyl, cycloalkylmethyl, aryl, substituted aryl, aralkyl or substituted aralkyl;

$R_a$, $R_g$, $R_{n'}$, and $R_o$ are independently H, alkyl, cycloalkyl, cycloalkylmethyl;

$R_t$ is —H, —COOH, —COOR$_k$, carbamoyl, or

where $R_k$ and $R_m$ are independently H, alkyl, cycloalkyl, cycloalkylmethyl;

$Y_1$ is H, amino or

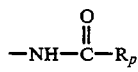

where $R_p$ is H, alkyl, cycloalkyl, cycloalkylmethyl, aryl, substituted aryl, aralkyl or substituted aralkyl;

x, x', x'', x''' and x'''' are independently 0 or 1; $m_1$ and $m_2$ are independently 0 to 9; $h_1$, $h_2$, and k are independently 0 or 1; n is 1 to 3; q is 1 to 5; and p and s are independently 0 to 6;

provided that when

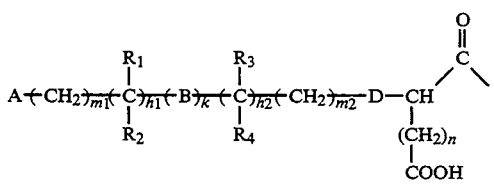

is arginyl-glycyl-aspartyl, then Z is other than a naturally occurring amino acid or a dipeptide composed of two naturally occurring amino acids;

and provided that Z is other than serine or a pharmaceutically acceptable salt thereof.

2. A compound of claim 1 wherein:

B and D are independently —CH$_2$—NH—, —CH$_2$—S—, —CH$_2$—O—,

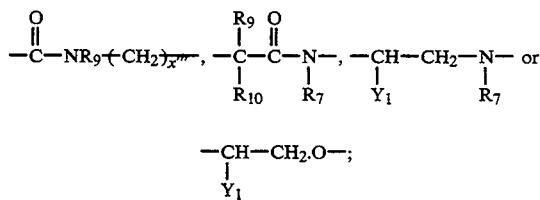

—CH—CH$_2$.O—;
|
Y$_1$

B may also be —CR$_7$=CR$_8$—; and

R$_z$ is —COOR$_n$, —OR$_n$, —SR$_n$—, —NR$_{n'}$R$_o$,

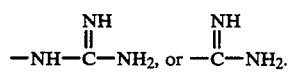

3. A compound of claim 2 wherein:

Z is —OR$_a$, a D- or L-isomer of an α-amino acid bonded at the α-nitrogen, a dipeptide bonded at the N-terminal α-amino acid, or —NR$_a$R$_x$ where R$_x$ is H or

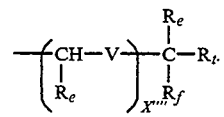

4. A compound of claim 1 of the formula

wherein:

A is guanidino or

[structure with N-N ring and R$_5$]

$m_1$ is 1 to 9;
$m_2$ is 0 or 1; and
B is —CH=CH— or $$-\overset{O}{\underset{\|}{C}}-NR_9(CH_2)_{x'''}-.$$

5. A compound of claim 4 wherein A is guanidino.

6. A compound of claim 5 wherein Z is a D- or L-isomer of an α-amino acid bonded at the α-nitrogen, or Z is a dipeptide bonded at the N-terminal α-amino acid.

7. A compound of claim 6 wherein Z is a D- or L-isomer of an α-amino acid bonded at the α-nitrogen.

8. A compound of claim 7 wherein the α-amino acid is selected from the group consisting of glycine, alanine, valine, leucine, isoleucine, serine, threonine, phenylalanine, tyrosine, tryptophan, cysteine, methionine, proline, hydroxyproline, aspartic acid, aspargine, glutamine, glutamic acid, histidine, arginine, ornithine, and lysine.

9. A compound of claim 8 wherein the α-amino acid is selected from the group consisting of valine, leucine, isoleucine, and arginine.

10. A compound of claim 1 which is:

5-guanidinopentanoyl-N-(ethyl)-glycyl-L-aspartyl-L-leucine or the trifluoroacetate salt thereof;

6-guanidinohexanoyl-N-(ethyl)-glycyl-L-aspartyl-L-leucine or the trifluoroacetate salt thereof;

6-guanidinohexanoyl-N-(ethyl)-glycyl-L-aspartyl-L-isoleucine or the trifluoroacetate salt thereof; or 6-guanidinohexanoyl-sarcosyl-L-aspartyl-L-leucine or the trifluoroacetate salt thereof;

or a pharmaceutically acceptable salt thereof.

11. A compound of claim 1 which is:

6-guanidinohexanoyl-N-(ethyl)-glycyl-L-aspartyl-L-valine or the trifluoroacetate salt thereof;

6-guanidinohexanoyl-sarcosyl-L-aspartyl-L-valine or the trifluoroacetate salt thereof; or 5-guanidinovaleroyl-sarcosyl-L-aspartyl-L-valine or the trifluoroacetate salt thereof;

or a pharmaceutically acceptable salt thereof.

12. A compound of claim 1 which is 5-guanidinopentanoyl-N-(ethyl)-glycyl-L-aspartyl-L-arginine or the ditrifluoroacetate salt thereof or a pharmaceutically acceptable salt thereof.

13. A compound of claim 1 which is 8-guanidinooct-2-enoyl-L-aspartyl-L-valine or the trifluoroacetate salt thereof or a pharmaceutically acceptable salt thereof.

14. A compound of claim 1 which is 9-guanidinononanoyl-L-aspartyl-L-isoleucine-4-guanidinobutyl amide or the ditrifluoroacetate salt thereof or a pharmaceutically acceptable salt thereof.

15. A compound of claim 1 which is 9-guanidinononanoyl-L-aspartyl-L-leucine or the trifluoroacetate salt thereof or a pharmaceutically acceptable salt thereof.

16. A compound of claim 1 which is 9-guanidinononanoyl-L-aspartyl-L-arginine or the difluoroacetate salt thereof or a pharmaceutically acceptable salt thereof.

17. A compound of claim 1 which is 9-guanidinononanoyl-L-aspartyl-L-arginine-isobutyl ester or the ditrifluoroacetate salt thereof or a pharmaceutically acceptable salt thereof.

18. A compound of claim 1 which is:
9-guanidinononanoyl-L-aspartyl-L-leucyl-arginine or the ditrifluoroacetate salt thereof;
9-guanidinononanoyl-L-aspartyl-L-valyl-arginine or the ditrifluoroacetate salt thereof;
N-[N-(9-guanidinononanoyl-L-aspartyl)-2-aminobutanoyl]-L-arginine or the ditrifluoroacetate salt thereof;
9-guanidinononanoyl-L-aspartyl-L-alanyl-arginine or the ditrifluoroacetate salt thereof;
9-guanidinononanoyl-L-aspartyl-L-norleucyl-arginine or the ditrifluoroacetate salt thereof;
9-guanidinononanoyl-L-aspartyl-D-homoisoleucyl-L-arginine or the ditrifluoroacetate salt thereof;
9-guanidinononanoyl-L-aspartyl-L-phenylalanyl-L-arginine or the ditrifluoroacetate salt thereof; or
N-(9-guanidinononanoyl-L-aspartyl)-3-amino-2-sec-butylpropionyl-L-arginine of the ditrifluoroacetate salt thereof; or
a pharmaceutically acceptable salt thereof.

19. A pharmaceutical composition for the prevention or treatment of abnormal thrombus formation in a mammal comprising a pharmaceutically acceptable carrier and an antithrombotic effective amount of a compound of claim 1.

20. A method for the prevention or treatment of abnormal thrombus formation in a mammal comprising the administration of a therapeutically effective amount of a compound of claim 1.

21. A method for the prevention or treatment of abnormal thrombus formation in a mammal comprising the administration of a therapeutically effective amount of the composition of claim 19.

* * * * *

UNITED STATES PATENT AND TRADEMARK OFFICE
CERTIFICATE OF CORRECTION

PATENT NO. : 5,332,726
DATED : July 26, 1994
INVENTOR(S) : Scott I. Klein, et al.

It is certified that error appears in the above-indentified patent and that said Letters Patent is hereby corrected as shown below:

On the title page, Item [75] Inventors, please delete "Jeffrey C. Pelletier, Lansdale".

Signed and Sealed this

Fifteenth Day of November, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,332,726
DATED : July 26, 1994
INVENTOR(S) : Klein et al.

It is certified that error appears in the above—identified patent and that said Letters Patent is hereby corrected as shown below:

Column 39, Line 50,

In Claim 1, the initial structure should appear as follows:

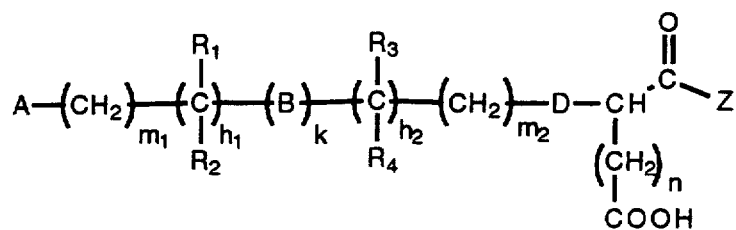

Signed and Sealed this

Fourteenth Day of November, 1995

Attest:

BRUCE LEHMAN

Attesting Officer    Commissioner of Patents and Trademarks